US011819843B2

(12) United States Patent
Khurana et al.

(10) Patent No.: US 11,819,843 B2
(45) Date of Patent: Nov. 21, 2023

(54) FLOW CELLS WITH A HYDROPHOBIC BARRIER

(71) Applicant: ILLUMINA, INC., San Diego, CA (US)

(72) Inventors: Tarun Kumar Khurana, Fremont, CA (US); Arnaud Rival, Saint Nazaire les Eymes (FR); Lewis J. Kraft, San Diego, CA (US); Steven Barnard, Del Mar, CA (US); M. Shane Bowen, Encinitas, CA (US); Xi-Jun Chen, San Carlos, CA (US); Yir-Shyuan Wu, Albany, CA (US); Jeffrey S. Fisher, San Diego, CA (US); Dajun Yuan, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 17/729,814

(22) Filed: Apr. 26, 2022

(65) Prior Publication Data

US 2022/0331792 A1    Oct. 20, 2022

Related U.S. Application Data

(62) Division of application No. 16/750,930, filed on Jan. 23, 2020, now Pat. No. 11,318,462.

(Continued)

(51) Int. Cl.
*B01L 3/00*    (2006.01)
*C12N 15/10*    (2006.01)
(Continued)

(52) U.S. Cl.
CPC .......... *B01L 3/5027* (2013.01); *B01L 3/5085* (2013.01); *C12N 15/1065* (2013.01); *B01L 3/5088* (2013.01); *B01L 2300/0896* (2013.01); *B01L 2300/161* (2013.01); *B01L 2300/165* (2013.01); *C08K 5/5406* (2013.01); *C08L 37/00* (2013.01)

(58) Field of Classification Search
CPC .... B01L 3/5027; B01L 3/5085; B01L 3/5088; B01L 2300/161; B01L 2300/165; B01L 3/502707; B01L 2200/12; B01L 2300/0819; B01L 2300/0893; B01L 2300/0896;
(Continued)

(56) References Cited

U.S. PATENT DOCUMENTS 7,794,799 B1 * 9/2010 Kim .................... B01J 19/0046
427/457
9,683,230 B2    6/2017 Gormley et al.
(Continued)

FOREIGN PATENT DOCUMENTS

EP          1600213 A1    11/2005
JP      2015084717 A     5/2015
(Continued)

*Primary Examiner* — Michael P LaPage
(74) *Attorney, Agent, or Firm* — Dierker & Kavanaugh, P.C.

(57) ABSTRACT

An example of a flow cell includes a substrate, which includes nano-depressions defined in a surface of the substrate, and interstitial regions separating the nano-depressions. A hydrophobic material layer has a surface that is at least substantially co-planar with the interstitial regions and is positioned to define a hydrophobic barrier around respective sub-sets of the nano-depressions.

10 Claims, 18 Drawing Sheets

Related U.S. Application Data

(60) Provisional application No. 62/798,356, filed on Jan. 29, 2019.

(51) Int. Cl.
*C08K 5/54* (2006.01)
*C08L 37/00* (2006.01)

(58) Field of Classification Search
CPC ........ B01L 2200/0663; C12N 15/1065; C08K 5/5406; C08L 37/00; C12Q 1/6869
See application file for complete search history.

(56) References Cited

U.S. PATENT DOCUMENTS

| | | | |
|---|---|---|---|
| 2002/0001546 A1* | 1/2002 | Hunter | B01L 3/5025 427/255.18 |
| 2004/0058423 A1* | 3/2004 | Albritton | G01N 27/44743 204/601 |
| 2004/0110211 A1 | 6/2004 | McCormick et al. | |
| 2004/0171166 A1* | 9/2004 | Hunter | G01N 21/75 436/164 |
| 2007/0269893 A1 | 11/2007 | Blankenstein et al. | |
| 2011/0130308 A1 | 6/2011 | Luckey et al. | |
| 2011/0212462 A1 | 9/2011 | Duffy et al. | |
| 2012/0308449 A1 | 12/2012 | Yang et al. | |
| 2012/0316086 A1 | 12/2012 | Lin et al. | |
| 2015/0044110 A1 | 2/2015 | Colombo et al. | |
| 2016/0167046 A1 | 6/2016 | Bramanti | |
| 2016/0318017 A1 | 11/2016 | Eltoukhy et al. | |
| 2016/0370319 A1 | 12/2016 | Molho et al. | |
| 2017/0130260 A1 | 5/2017 | Rigatti et al. | |
| 2017/0157641 A1* | 6/2017 | Niemeyer | B05D 3/06 |
| 2018/0067113 A1 | 3/2018 | Kunding | |
| 2018/0087100 A1 | 3/2018 | Otsuka et al. | |
| 2018/0104686 A1 | 4/2018 | Watanabe et al. | |
| 2018/0155709 A1 | 6/2018 | Gormley et al. | |
| 2018/0195950 A1 | 7/2018 | Tsay et al. | |
| 2018/0245069 A1 | 8/2018 | Desantis et al. | |
| 2018/0250672 A1* | 9/2018 | Jamshidi | B01L 3/5088 |
| 2018/0273933 A1 | 9/2018 | Gunderson et al. | |
| 2020/0261877 A1* | 8/2020 | Watanabe | A61K 9/1277 |
| 2020/0262113 A1 | 8/2020 | Okashita et al. | |

FOREIGN PATENT DOCUMENTS

| | | |
|---|---|---|
| KR | 100455293 B1 | 10/2004 |
| WO | 2001091855 A1 | 12/2001 |
| WO | 2003072831 A1 | 9/2003 |
| WO | 2014133905 A1 | 9/2014 |
| WO | 2015183871 A1 | 12/2015 |
| WO | 2016061517 A2 | 4/2016 |
| WO | 2016075204 A1 | 5/2016 |
| WO | 2016159068 A1 | 10/2016 |
| WO | 2016161400 A1 | 10/2016 |
| WO | 2016168386 A1 | 10/2016 |
| WO | 2017030999 A1 | 2/2017 |
| WO | 2017201198 A1 | 11/2017 |
| WO | 2018119053 A1 | 6/2018 |
| WO | 2018125982 A1 | 7/2018 |

* cited by examiner

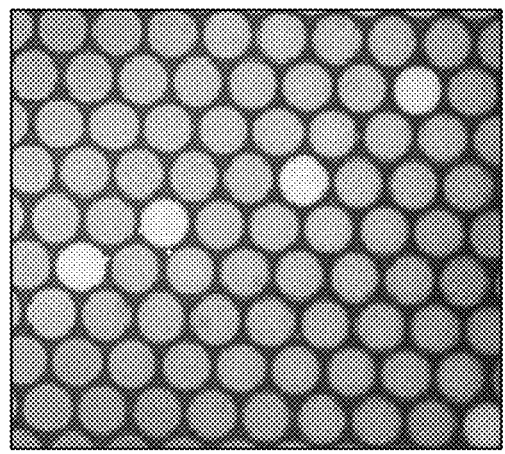
FIG. 14C(i)
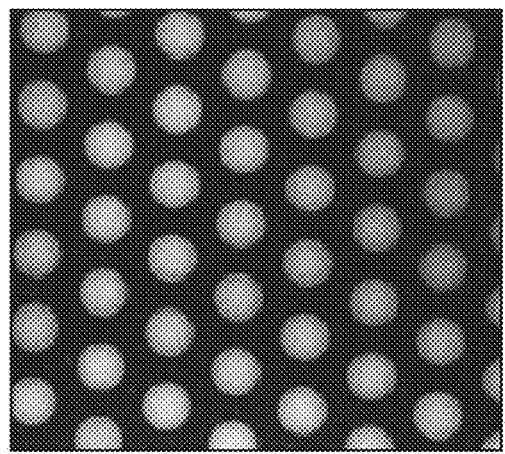
FIG. 14B(i)
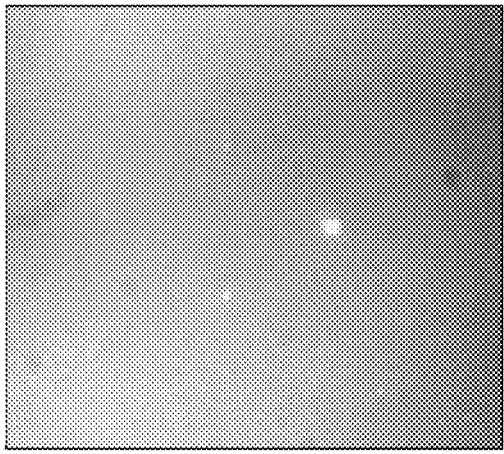
FIG. 14A(i)
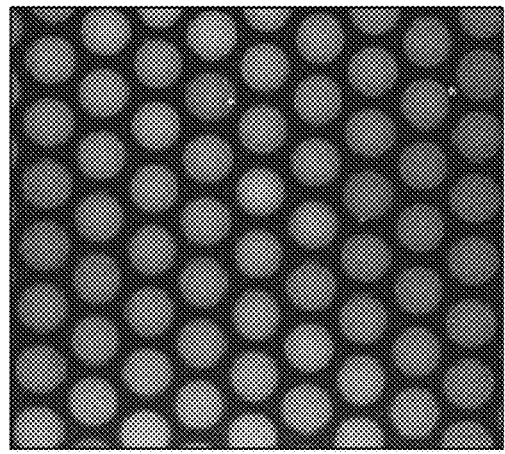
FIG. 14C(ii)
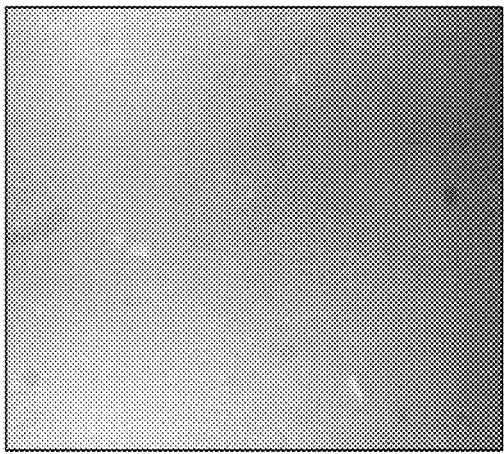
FIG. 14B(ii)
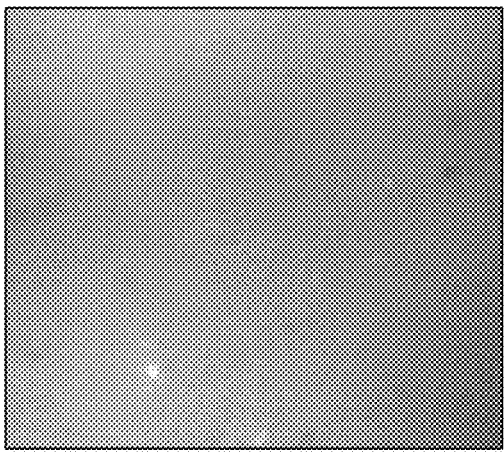
FIG. 14A(ii)

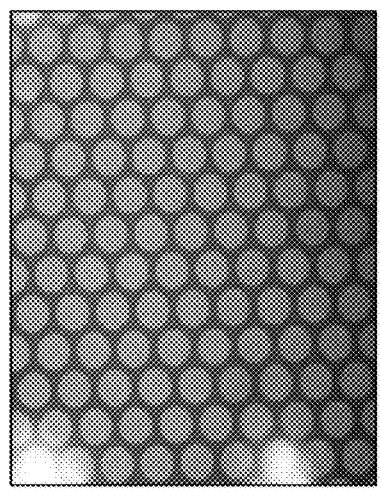 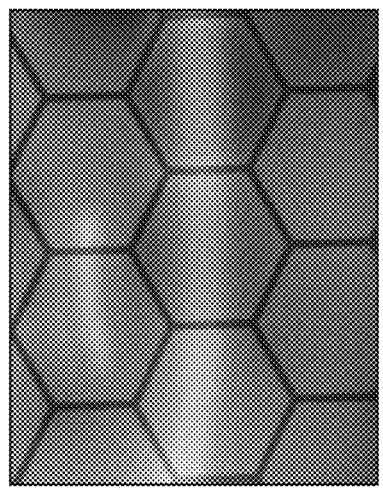
FIG. 16A    FIG. 16B
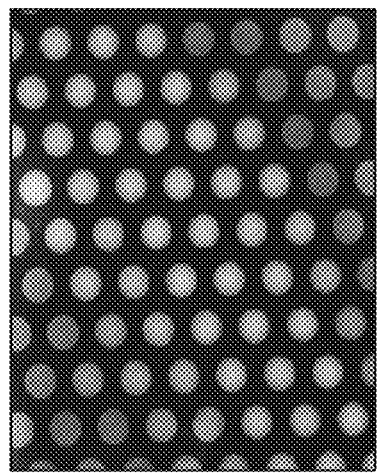 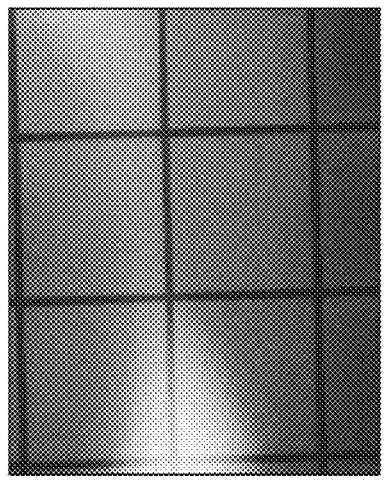
FIG. 16C    FIG. 16D
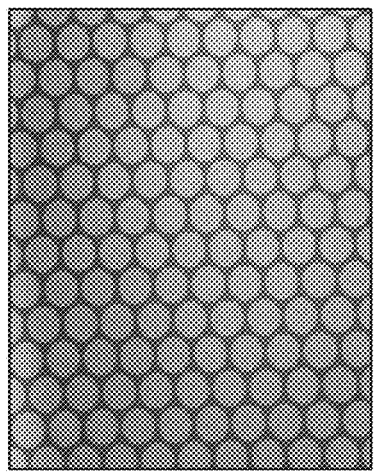
FIG. 16E

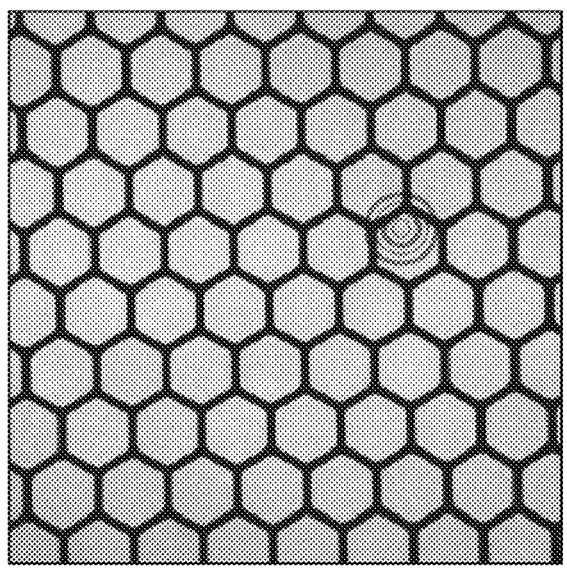 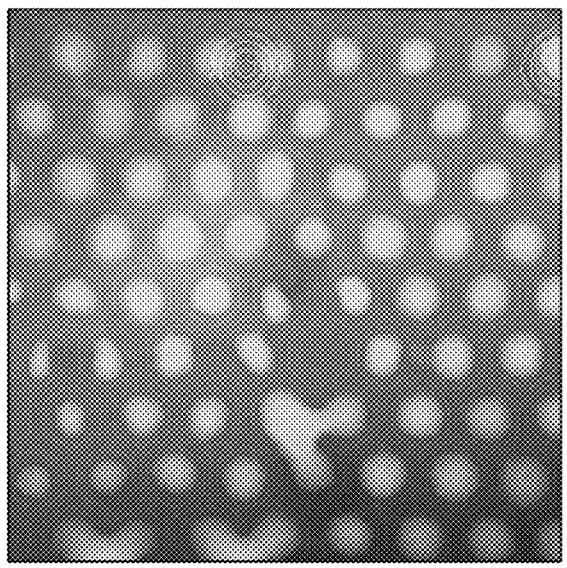
FIG. 18A  FIG. 18B
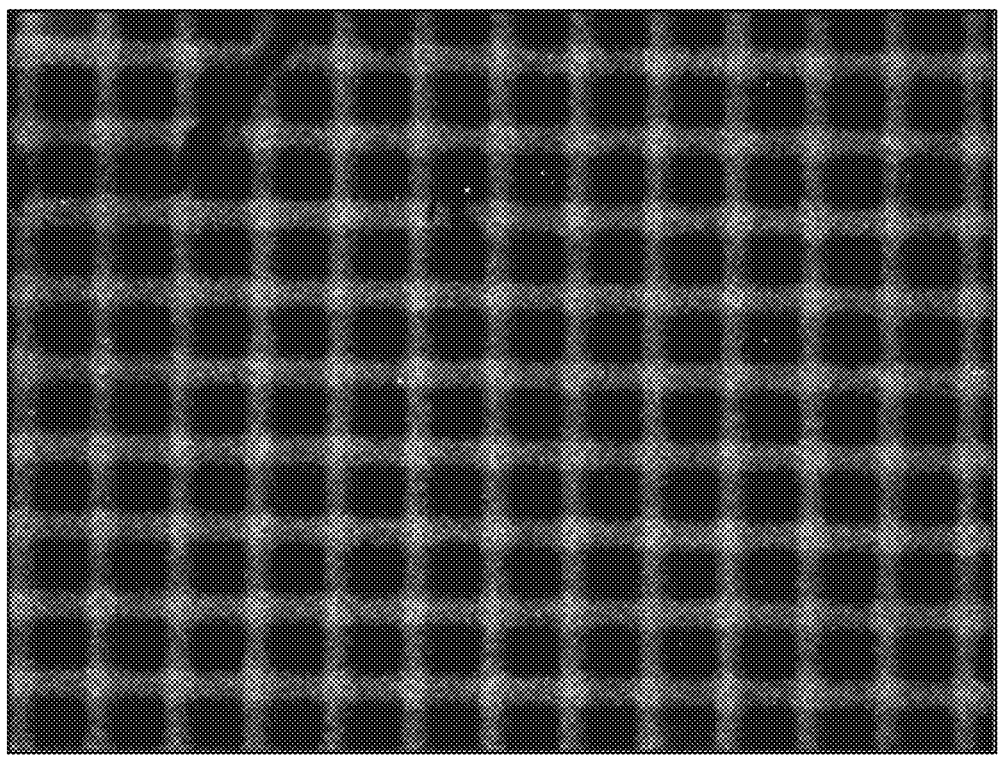
FIG. 19

FLOW CELLS WITH A HYDROPHOBIC BARRIER

CROSS-REFERENCE TO RELATED APPLICATIONS

This application is a divisional of U.S. application Ser. No. 16/750,930, filed Jan. 23, 2020, which itself claims the benefit of U.S. Provisional Application Ser. No. 62/798,356, filed Jan. 29, 2019; the content of each of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing. With polynucleotide sequencing techniques, the analysis may help identify or reveal properties of the polynucleotide involved in the reactions.

INTRODUCTION

A first aspect disclosed herein is a flow cell comprising: a substrate including: nano-depressions defined in a surface of the substrate; and interstitial regions separating the nano-depressions; and a hydrophobic material layer i) having a surface that is at least substantially co-planar with the interstitial regions and ii) positioned to define a hydrophobic barrier around respective sub-sets of the nano-depressions.

In an example of the first aspect, the substrate further includes a barrier interstitial surrounding each of the respective sub-sets of the nano-depressions; an the hydrophobic material layer is defined on the barrier interstitial and has a thickness less than about 2 µm.

In an example of the first aspect, the substrate further includes a barrier depression surrounding each of the respective sub-sets of the nano-depressions; and the hydrophobic material layer is positioned in the barrier depression.

In an example of the first aspect, the hydrophobic material layer has a thickness ranging from about 10 nm to about 1 µm.

In an example of the first aspect, the hydrophobic material is selected from the group consisting of a fluorinated polymer, a perfluorinated polymer, a silicon polymer, a silane, and a mixture thereof.

In an example of the first aspect, the flow cell further comprises a polymer layer in the nano-depressions; and a primer attached to the polymer layer.

It is to be understood that any features of the flow cell disclosed herein may be combined together in any desirable manner and/or configuration.

A second aspect disclosed herein is a method comprising: applying a hydrophobic material on a patterned substrate, including: nano-depressions defined in a surface of the patterned substrate; and interstitial regions separating the nano-depressions; thereby forming a hydrophobic material layer i) in the nano-depressions and ii) on the interstitial regions, wherein the hydrophobic material layer on the interstitial regions has a thickness less than about 2 µm; applying a mask material on a first portion of the hydrophobic material layer to define a pattern of a hydrophobic barrier around respective sub-sets of the nano-depressions and the interstitial regions, whereby a second portion of the hydrophobic material layer is exposed at the respective sub-sets; removing the second portion of the hydrophobic material layer, thereby exposing the respective sub-sets of the nano-depressions and the interstitial regions; attaching a gel material to the nano-depressions of the respective sub-sets; and removing the mask material from the first portion of the hydrophobic material layer to reveal the hydrophobic barrier.

In an example of the second aspect, the patterned substrate further includes a barrier interstitial around the respective sub-sets of the nano-depressions and the interstitial regions; and the hydrophobic barrier is formed on the barrier interstitial.

In an example of the second aspect, the hydrophobic barrier is formed in some of the nano-depressions and on some of the interstitial regions that are positioned between the respective sub-sets of the nano-depressions and the interstitial regions.

In an example of the second aspect, the attaching of the gel material involves: silanizing the nano-depressions and interstitial regions of the respective sub-sets; and depositing the gel material on the nano-depressions and interstitial regions of the respective sub-sets and on the mask material; and the method further comprises removing the gel material from the mask material and from the interstitial regions of the respective sub-sets.

In an example of the second aspect, the hydrophobic material is selected from the group consisting of a fluorinated polymer, a perfluorinated polymer, a silicon polymer, and a mixture thereof.

In an example of the second aspect, prior to applying the hydrophobic material, the method further comprises forming the patterned substrate by patterning a non-patterned support to form the nano-depressions. In an example, the patterning involves etching, nano-imprint lithography, or combinations thereof.

In an example of the second aspect, the removing of the mask material from the first portion of the hydrophobic material layer to reveal the hydrophobic barrier occurs prior to attaching the gel material; and attaching the gel material involves: silanizing the nano-depressions and interstitial regions of the respective sub-sets; and depositing the gel material on the nano-depressions and interstitial regions of the respective sub-sets and on the hydrophobic barrier; and the method further comprises removing the gel material from the hydrophobic barrier and from the interstitial regions of the respective sub-sets.

It is to be understood that any features of this method may be combined together in any desirable manner. Moreover, it is to be understood that any combination of features of the method and/or of the flow cell may be used together, and/or combined with any of the examples disclosed herein.

A third aspect disclosed herein is a method comprising: applying a hydrophobic material on a patterned substrate, including: sub-sets of nano-depressions defined in a surface of the patterned substrate and separated by interstitial regions; and a barrier depression defined in the surface of the patterned substrate around each of the sub-sets; thereby forming a hydrophobic material layer i) in the barrier depression and ii) in the nano-depressions; applying a mask material on the hydrophobic material layer in the barrier depression; removing the hydrophobic material layer from the nano-depressions; attaching a gel material to the nano-depressions of the sub-sets; and removing the mask material from the hydrophobic material layer in the barrier depression to reveal a hydrophobic barrier.

In an example of the third aspect, the attaching of the gel material involves: silanizing the nano-depressions and the interstitial regions of the sub-sets; and depositing the gel material on the nano-depressions and the interstitial regions of the sub-sets and on the mask material; and the method further comprises removing the gel material from the mask material and from the interstitial regions.

In an example of the third aspect, the hydrophobic material is selected from the group consisting of a fluorinated polymer and a polysiloxane.

In an example of the third aspect, wherein prior to applying the hydrophobic material, the method further comprises forming the patterned substrate by patterning a non-patterned support to form the nano-depressions and the barrier depression. In an example, the patterning involves etching, nano-imprint lithography, or combinations thereof.

It is to be understood that any features of the method may be combined together in any desirable manner. Moreover, it is to be understood that any combination of features of this method and/or of the other method and/or of the flow cell may be used together, and/or combined with any of the examples disclosed herein.

A fourth aspect disclosed herein is a method comprising applying a hydrophobic material on a patterned substrate, including: sub-sets of nano-depressions defined in a surface of the patterned substrate and separated by interstitial regions, the nano-depressions having a first depth; and a barrier depression defined in the surface of the patterned substrate around each of the sub-sets, the barrier depression having a second depth that is greater than the first depth; thereby introducing the hydrophobic material i) into the barrier depression and ii) into the nano-depressions; removing the hydrophobic material at least from the nano-depressions, whereby at least some of the hydrophobic material remains in the barrier depression; and curing the at least some of the hydrophobic material that remains in the barrier depression.

In an example of the fourth aspect, the method further comprises attaching a gel material to the nano-depressions by: silanizing the nano-depressions and the interstitial regions of the sub-sets; and depositing the gel material on the nano-depressions and the interstitial regions of the sub-sets; and removing the gel material from the interstitial regions.

In an example of the fourth aspect, the hydrophobic material is selected from the group consisting of a fluorinated polymer, a perfluorinated polymer, a silicon polymer, and a mixture thereof.

In an example of the fourth aspect, prior to applying the hydrophobic material, the method further comprises forming the patterned substrate by patterning a non-patterned support to form the nano-depressions and the barrier depression. In an example, the patterning involves etching, nano-imprint lithography, or combinations thereof.

It is to be understood that any features of the method may be combined together in any desirable manner. Moreover, it is to be understood that any combination of features of this method and/or of the other methods and/or of the flow cell may be used together, and/or combined with any of the examples disclosed herein.

A fifth aspect disclosed herein is a method comprising: applying a mask material on a patterned substrate, including: nano-depressions defined in a surface of the patterned substrate; interstitial regions separating the nano-depressions; and a gel material in the nano-depressions; thereby defining a pattern for a hydrophobic barrier around respective sub-sets of the nano-depressions and the interstitial regions; applying a hydrophobic material layer according to the pattern, thereby forming the hydrophobic barrier, wherein the hydrophobic material layer has a thickness less than about 2 μm; and removing the mask material.

In an example of the fifth aspect, the hydrophobic material layer is also applied on the mask material, and wherein removing the mask material removes the hydrophobic material layer thereon.

In an example of the fifth aspect, the applying of the mask material includes: applying a bi-layer resist on the patterned substrate, the bi-layer resist including a lift-off layer and an imaging layer; defining the pattern in the imaging layer, thereby exposing portions of the lift-off layer; and removing the exposed portions of the lift-off layer.

In an example of the fifth aspect, the hydrophobic material is selected from the group consisting of a fluorinated polymer, a perfluorinated polymer, a silicon polymer, and a mixture thereof.

In an example of the fifth aspect, wherein prior to applying the mask material, the method further comprises forming the patterned substrate by: patterning a non-patterned support to form the nano-depressions; attaching the gel material to the nano-depressions by silanizing the nano-depressions and the interstitial regions; depositing the gel material on the nano-depressions and the interstitial regions; and removing the gel material from the interstitial regions.

It is to be understood that any features of the method may be combined together in any desirable manner. Moreover, it is to be understood that any combination of features of this method and/or of the other methods and/or of the flow cell may be used together, and/or combined with any of the examples disclosed herein.

A sixth aspect disclosed herein is a method comprising laminating a hydrophobic material film having a thickness less than about 2 μm to a patterned substrate, including: nano-depressions defined in a surface of the patterned substrate; interstitial regions separating the nano-depressions; and a gel material in the nano-depressions; and exposing the dry hydrophobic material film to photolithography to form a hydrophobic barrier around respective sub-sets of the nano-depressions and the interstitial regions.

In an example of the sixth aspect, the hydrophobic material film is selected from the group consisting of a fluorinated polymer, a perfluorinated polymer, a silicon polymer, a silane, and a mixture thereof.

In an example of the sixth aspect, wherein prior to laminating the hydrophobic material film, the method further comprises forming the patterned substrate by: patterning a non-patterned support to form the nano-depressions; and attaching the gel material to the nano-depressions by: silanizing the nano-depressions and the interstitial regions; depositing the gel material on the nano-depressions and the interstitial regions; and removing the gel material from the interstitial regions.

It is to be understood that any features of the method may be combined together in any desirable manner. Moreover, it is to be understood that any combination of features of this method and/or of the other methods and/or of the flow cell may be used together, and/or combined with any of the examples disclosed herein.

A seventh aspect disclosed herein is a method comprising printing a hydrophobic material to a patterned substrate, including: nano-depressions defined in a surface of the patterned substrate; interstitial regions separating the nano-depressions; and a gel material in the nano-depressions; wherein the hydrophobic material is printed to form a hydrophobic barrier around respective sub-sets of the nano-depressions and the interstitial regions and to have a thickness less than about 2 μm.

In an example of the seventh aspect, the hydrophobic material is selected from the group consisting of a fluorinated polymer, a perfluorinated polymer, a silicon polymer, a silane, and a mixture thereof.

In an example of the seventh aspect, wherein prior to printing the hydrophobic material, the method further comprises forming the patterned substrate by: patterning a non-patterned support to form the nano-depressions; and attaching the gel material to the nano-depressions by: silanizing the nano-depressions and the interstitial regions; depositing the gel material on the nano-depressions and the interstitial regions; and removing the gel material from the interstitial regions.

In an example of the seventh aspect, the printing involves aerosol printing.

It is to be understood that any features of the method may be combined together in any desirable manner. Moreover, it is to be understood that any combination of features of this method and/or of the other methods and/or of the flow cell may be used together, and/or combined with any of the examples disclosed herein.

An eighth aspect disclosed herein is a method comprising laser cutting and weeding a multi-layer precursor including: two sacrificial layers; and a hydrophobic material layer having a thickness less than about 2 μm positioned between the two sacrificial layers; thereby removing a first of the two sacrificial layers and defining a pattern of a hydrophobic barrier in the hydrophobic material layer that is positioned on a second of the two sacrificial layers; laminating the patterned hydrophobic material to a patterned substrate, including: nano-depressions defined in a surface of the patterned substrate; interstitial regions separating the nano-depressions; and a gel material in the nano-depressions.

In an example of the eighth aspect, the method further comprises removing the second of the two sacrificial layers.

In an example of the eighth aspect, the hydrophobic material is selected from the group consisting of a fluorinated polymer, a perfluorinated polymer, a silicon polymer, a silane, and a mixture thereof.

In an example of the eighth aspect, wherein prior to printing the hydrophobic material, the method further comprises forming the patterned substrate by: patterning a non-patterned support to form the nano-depressions; and attaching the gel material to the nano-depressions by: silanizing the nano-depressions and the interstitial regions; depositing the gel material on the nano-depressions and the interstitial regions; and removing the gel material from the interstitial regions.

It is to be understood that any features of the method may be combined together in any desirable manner. Moreover, it is to be understood that any combination of features of this method and/or of the other methods and/or of the flow cell may be used together, and/or combined with any of the examples disclosed herein.

A ninth aspect disclosed herein is a method comprises coating a stamp with a hydrophobic material, the stamp defining a pattern of a hydrophobic barrier; and transferring the hydrophobic material in the pattern of the hydrophobic barrier to a patterned substrate, including: nano-depressions defined in a surface of the patterned substrate; interstitial regions separating the nano-depressions; and a gel material in the nano-depressions; thereby forming the hydrophobic barrier around respective sub-sets of the nano-depressions and the interstitial regions, the hydrophobic barrier having a thickness less than about 2 μm.

In an example of the ninth aspect, the hydrophobic material is selected from the group consisting of a fluorinated polymer, a perfluorinated polymer, a silicon polymer, a silane, and a mixture thereof.

In an example of the ninth aspect, wherein prior to transferring the hydrophobic material, the method further comprises forming the patterned substrate by: patterning a non-patterned support to form the nano-depressions; and attaching the gel material to the nano-depressions by: silanizing the nano-depressions and the interstitial regions; depositing the gel material on the nano-depressions and the interstitial regions; and removing the gel material from the interstitial regions.

It is to be understood that any features of the method may be combined together in any desirable manner. Moreover, it is to be understood that any combination of features of this method and/or of the other methods and/or of the flow cell may be used together, and/or combined with any of the examples disclosed herein.

In a tenth aspect, another example of a flow cell comprises a substrate; nano-pads of a gel material positioned on the substrate; and a hydrophobic material layer i) having a surface that is at least substantially co-planar with a surface of the nano-pads and ii) positioned to define a hydrophobic barrier around respective sub-sets of the nano-pads.

In an example of the tenth aspect, each of the nano-pads has a thickness less than about 2 μm; and the hydrophobic material layer has a thickness less than about 2 μm.

In an example of the tenth aspect, the flow cell further comprises a plurality of primers attached to each of the nano-pads.

It is to be understood that any features of this flow cell may be combined together in any desirable manner. Moreover, it is to be understood that any combination of features of this flow cell and/or of the methods and/or of the other flow cell may be used together, and/or combined with any of the examples disclosed herein.

In an eleventh aspect, another example of a method comprises forming discrete subsets of nano-pads on a substrate, each of the nano-pads having a thickness less than about 2 μm; and selectively applying a hydrophobic material on the substrate around each of the discrete subsets, thereby forming a hydrophobic barrier i) around each of the discrete subsets, ii) having a surface that is at least substantially co-planar with a surface of the nano-pads, and iii) having a thickness less than about 2 μm.

In an example of the eleventh aspect, the selectively applying of the hydrophobic material involves transferring the hydrophobic material in a pattern of the hydrophobic barrier to the substrate.

In another example of the eleventh aspect, the selectively applying of the hydrophobic material involves printing the hydrophobic material in a pattern of the hydrophobic barrier to the substrate.

In still another example of the eleventh aspect, the selectively applying of the hydrophobic material involves applying a mask material on the discrete subsets of nano-pads, thereby defining a pattern for the hydrophobic barrier; applying the hydrophobic material according to the pattern, thereby forming the hydrophobic barrier; and removing the mask material.

In an example of the eleventh aspect, the forming of the discrete subsets of nano-pads involves applying a gel material on a surface of the substrate; disposing a mask material on the gel material; forming spaces in the mask material and the gel material; and removing the mask material.

It is to be understood that any features of this method may be combined together in any desirable manner. Moreover, it is to be understood that any combination of features of this method and/or of the other methods and/or of the flow cells may be used together, and/or combined with any of the examples disclosed herein.

Still further, it is to be understood that any features of any of the methods and/or of any of the flow cells may be combined together in any desirable manner, and/or may be combined with any of the examples disclosed herein at least to achieve the benefits as described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 14A(i) and (ii), 14B(i) and (ii), and 14C(i) and (ii) are black and white fluorescence microscopy images of flow cells including examples of the micro-chamber geometries disclosed herein when a fluid was introduced thereto (top images, namely 14A(i), 14B(i), and 14C(i)) and when aspiration was performed (bottom images, namely 14A(ii), 14B(ii), and 14C(ii));

FIGS. 16A through 16E are black and white fluorescence microscopy images of different examples of the micro-chamber geometries defined by respective hydrophobic material layers having a thickness of about 1 µm, after aspiration was performed;

FIGS. 18A and 18B are black and white fluorescence microscopy images of an example hexagonal micro-chamber geometry defined by a hydrophobic material layer A) after fluorescent labeled primers were grafted and B) after the fluorescent liquid as displaced with oil; and FIG. 19 is a micrograph of example micro-chambers defined by a printed hydrophobic material layer.

DETAILED DESCRIPTION

Figure 1:
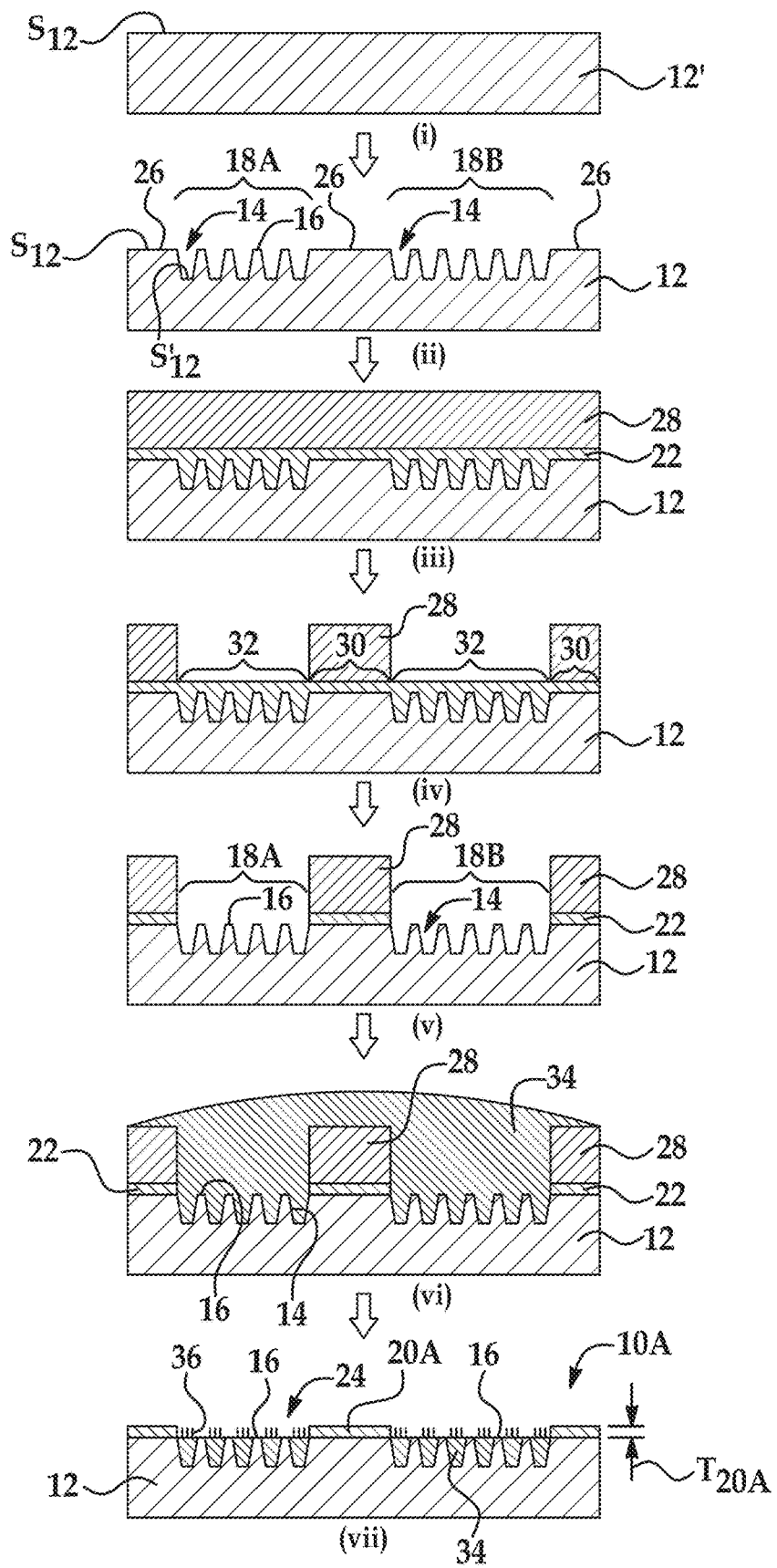
FIG. 1 is a schematic flow diagram including (i) through (vii) illustrating one example of the methods disclosed herein to form one example of the flow cell disclosed herein.

Some examples of the flow cells disclosed herein include a patterned substrate having nano-depressions separated by interstitial regions. In these examples, a hydrophobic material layer, that is at least substantially co-planar with the interstitial regions, defines a perimeter around one or more sub-sets of the nano-depressions. Other examples of the flow cells disclosed herein include a substrate having nano-pads of a gel material positioned on the substrate. In these examples, the hydrophobic material layer is at least substantially co-planar with a surface of the nano-pads and defines a perimeter around one or more sub-sets of the nano-pads. In all of the examples, the hydrophobic material layer creates a hydrophobic barrier around the sub-set(s). During use of the flow cell, the hydrophobic barrier can help guide more hydrophilic reagents and samples toward the sub-set(s) of nano-depressions or nano-pads. As a result, reagents and samples can more effectively reach reaction areas (e.g., the nano-depressions or the nano-pads), and can help reduce or eliminate reagent and sample residue and/or contamination across the flow cell. During a sequencing reaction, the hydrophobic barrier can also prevent a sequencing library that is released within the barrier from diffusing outside of the barrier.

As mentioned, in some examples, the hydrophobic material layer is at least substantially co-planar with the interstitial regions; and in other examples, the hydrophobic material layer is at least substantially co-planar with a surface of the nano-pads. By "at least substantially co-planar", it is meant that a surface of the hydrophobic material layer does not extend outward in the Z-direction more than 2 µm beyond a surface of the interstitial regions or the surface of the nano-pads. The Z-direction refers to the Z-axis of the Cartesian coordinate system for a three-dimensional space. In some instances, the hydrophobic material layer and the interstitial regions or nano-pad surfaces are substantially co-planar. In one example where the interstitial regions and the hydrophobic material layer are substantially co-planar, the hydrophobic material layer may be a monolayer, e.g., on the order of about 10 Angstroms. In other instances, the hydrophobic material layer and the interstitial regions are or nano-pad surfaces co-planar. The substantially co-planar hydrophobic material layer does not affect auto-focusing during imaging. Additionally, when the hydrophobic material layer does extend outward in the Z-direction higher than the interstitial regions or the nano-pad surfaces, the thickness of the higher portion (e.g., the portion of the hydrophobic material layer that extends above the interstitial regions or the nano-pad surfaces) may be too thin for the sequencing library to seed on the sidewalls of the hydrophobic material layer. Thus, in some examples, loss of the sequencing library to the sidewalls of the hydrophobic material layer is at least reduced compared to loss that may be exhibited with thicker sidewalls. As examples, the thickness of the portion the hydrophobic material layer that extends above the interstitial regions or the nano-pad surfaces is less than 2 µm. In some examples, the thickness of the portion of the hydrophobic material layer that extends above the interstitial regions or the nano-pad surfaces ranges from about 20 nm to about 2 µm—e.g., from about 10 nm to about 100 nm, from about 100 nm to about 1 µm, or from about 1 µm to about 2 µm. Other values are also possible.

The hydrophobic material used in the methods disclosed herein may include any material that repels or fails to mix with water.

Definitions

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, non-recited elements or method steps.

Reference throughout the specification to "one example", "another example", "an example", and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Adapter. A linear oligonucleotide sequence that can be fused to a nucleic acid molecule, for example, by ligation or tagmentation. In some examples, the adapter is substantially non-complementary to the 3' end or the 5' end of any target sequence introduced to the flow cell. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter includes one or more cleavable groups at one or more locations. In some examples, the adapter can include a sequence that is complementary to at least a portion of a primer, for example, a primer including a universal nucleotide sequence (such as a P5 or P7 sequence). In some examples, the adapter can include an index or barcode sequence that assists in downstream error correction, identification, or sequencing. The index may be unique to a sample or source of the nucleic acid molecule (e.g., a fragment). In some examples, the adapter can include a sequencing primer sequence or sequencing binding site. Combinations of different adapters may be incorporated into a nucleic acid molecule, such as a DNA fragment.

Capture site: A portion of a flow cell surface having been physically modified and/or modified with a chemical property that allows for localization of a complex. In an example, the capture site may include a chemical capture agent.

Carrier. A hydrogel support that is capable of having a sequencing library contained therein or a solid support capable of having a sequencing-ready nucleic acid fragments attached to a surface thereof.

Chamber: A portion of the flow cell that is within a perimeter defined by a hydrophobic barrier. Because the hydrophobic barrier defines the perimeter of the chamber, the chamber may not have physical sidewalls, or may have sidewalls that are less than 2 µm tall.

Chemical capture agent: A material, molecule or moiety that is capable of attaching, retaining, or binding to a target molecule (i.e., a complex). One example chemical capture agent includes a capture nucleic acid (e.g., a capture oligonucleotide) that is complementary to at least a portion of a target nucleic acid of or attached to the target molecule. Still another example chemical capture agent includes a member of a receptor-ligand binding pair (e.g., avidin, streptavidin, biotin, lectin, carbohydrate, nucleic acid binding protein, epitope, antibody, etc.) that is capable of binding to the target molecule (or to a linking moiety attached to the target molecule). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target molecule.

Complex: A carrier, such as a hydrogel support or a solid support, and sequencing-ready nucleic acid fragments attached to or contained within the carrier. The carrier may also include one member of a binding pair whose other member is part of the capture site.

External immobilizing agent: A gaseous, liquid or viscous medium that is not miscible with a complex that has been introduced to the flow cell chambers. The gaseous external immobilizing agent may be used to create a droplet around a complex. An example of a gaseous external immobilizing agent is air that is directed at a suitable flow rate through the flow cell. For example, air may be used to aspirate a fluid containing a complex from the flow cell, which forms droplets of the liquid containing the complex or sample. The formed droplet acts as a diffusion barrier. The liquid or viscous medium is used to prevent diffusion of a sequencing library released from a complex. The external immobilizing agent can form a diffusion barrier, as the sequencing libraries or any other polynucleotide have little to no solvation in the external immobilizing agent. Example external immobilizing agents in liquid form include hydrophobic oils, such as mineral oil, silicone oil, perfluorinated oil, a fluorinated carbon oil (e.g., FLUORINERT™ FC40 from 3M), or a combination thereof. Example external immobilizing agents in viscous medium form include buffers containing polymers (e.g., polyethylene glycol, polyvinylpyrrolidone, etc.), dextran, sucrose, glycerol, and the like. In some examples, the viscous medium is a temperature responsive gel. The temperature responsive gel is non-viscous at non-seeding temperatures, and turns into a viscous medium at seeding temperatures. Examples of temperature responsive gels include poly(N-isopropylacrylamide) and polyethylene oxide-polypropylene oxide-polyethylene oxide (PEO-PPO-PEO)/laponite nanoparticle composites.

Fragment: A portion or piece of genetic material (e.g., DNA, RNA, etc.).

Hydrogel or hydrogel matrix: A colloid material including an organic polymer (natural or synthetic) that is cross-linked via covalent, ionic, or hydrogen bonds to create a three-dimensional open-lattice structure that entraps water molecules to form the gel. In an example, the hydrogel include from about 60% to about 90% fluid, such as water, and from about 10% to about 30% polymer. The hydrogel may be porous, i.e., including open/void space. The porosity is a fractional volume (dimensionless) of the hydrogel, i.e., measures void space in a material and is a fraction of the volume of voids over the total volume, as a percentage between 0 and 100% (or a fraction between 0 and 1). In an example, the porosity of the hydrogel may range from about 50% (0.5) to about 99% (0.99). The porosity may be sufficient to allow diffusion of reagents (e.g., enzymes, chemicals, and smaller sized oligonucleotides (less than 50 base pairs, e.g., primers), but prohibits diffusion of larger sized nucleic acid molecules (e.g., samples, fragments, etc.)

Hydrogel support: A hydrogel having an at least substantially spherical shape (e.g., a hydrogel bead) that can contain a sequencing library therein.

Hydrophobic barrier. A layer of a hydrophobic material that is applied on a substrate surface or in a depression in a configuration that surrounds a sub-set of nano-depressions.

Nucleic acid molecule: A polymeric form of nucleotides of any length, and may include ribonucleotides, deoxyribonucleotides, analogs thereof, or mixtures thereof. The term may refer to single stranded or double stranded polynucleotides.

A "target" or "template" nucleic acid molecule may refer to a sequence that is to be analyzed.

The nucleotides in a nucleic acid molecule may include naturally occurring nucleotides and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNS can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Primer. A nucleic acid molecule that can hybridize to a target sequence of interest. In an example, the primer functions as a substrate onto which nucleotides can be polymerized by a polymerase. For example, an amplification primer serves as a starting point for template amplification and cluster generation. In still another example, the primer can serve as a starting point for DNA or RNA synthesis. For example, a sequencing primer can hybridize to a synthesized nucleic acid template strand in order to prime synthesis of a new strand that is complementary to the synthesized nucleic acid template strand. The primer can include any combination of nucleotides or analogs thereof. In some examples, the primer is a single-stranded oligonucleotide or polynucleotide.

Sample: Any source of genetic material, such as cells, microbiomes, or nucleic acids. In some examples, the cell is a single cell including a prokaryotic or a eukaryotic cell. In some examples, the cell is a mammalian cell, a human cell, or a bacterial cell. In some examples, the nucleic acid is a long DNA molecule, including viral nucleic acids, bacterial nucleic acids, or mammalian nucleic acids. In some examples, the sample is bound (as fragments) via insertion, e.g., to transposons bound to the surface of a solid support (e.g., bead).

Sequencing-ready nucleic acid fragments: A portion (fragment) of genetic material having adapters at the 3' and 5' ends. In the sequencing-ready nucleic acid fragment, each adapter includes a known universal sequence (e.g., which is complementary to at least a portion of a primer on a flow cell) and a sequencing primer sequence. Both of the adapters may also include an index (barcode or tag) sequence. In an example, the P5 side may contain a bead index and the P7 side may contain a sample index. A sequencing-ready nucleic acid fragment may be bound via insertion of transposons bound to the surface of a solid support (e.g., bead), or directly immobilized through a binding pair or other cleavable linker. A sequencing-ready nucleic acid fragment may also be contained within a hydrogel support.

Seeding: Immobilization of adapted fragments (e.g., sequencing-ready nucleic acid fragments) in a chamber of an example of the flow cells disclosed herein.

Sequencing library: A collection of nucleic acid fragments of one or more target nucleic acid molecules, or amplicons of the fragments. In some examples, the fragments are linked to one or more adapters at their 3' and 5' ends. In some examples, a sequencing library is prepared from one or more target nucleic acid molecules and is part of a complex. In other examples, a sequencing library is prepared on a flow cell surface using a sample.

Solid support: A small body made of a rigid or semi-rigid material having a shape characterized, for example, as a sphere, oval, microsphere, or other recognized particle shape whether having regular or irregular dimensions. The solid support can have a sequencing library attached thereto. Example materials that are useful for the solid support include, without limitation, glass; plastic, such as acrylic, polystyrene or a copolymer of styrene and another material, polypropylene, polyethylene, polybutylene, polyurethane or polytetrafluoroethylene (such as TEFLON® from The Chemours Co); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers. Example solid supports include controlled pore glass beads, paramagnetic or other magnetic beads, thoria sol, Sepharose beads, nanocrystals and others known in the art as described, for example, in Microsphere Detection Guide from Bangs Laboratories, Fishers Ind.

Tagmentation: Modification of a nucleic acid molecule (e.g., a DNA or RNA sample) by a transposome to fragment the nucleic acid molecule and ligate adapters to the 5' and 3' ends of the fragment in a single step. Tagmentation reactions may be used to prepare sequencing libraries, in particular, complexes that include the solid support. Tagmentation reactions combine random sample fragmentation and adapter ligation into a single step, which increases the efficiency of the sequencing library preparation process.

Transposome: A complex formed between an integration enzyme (e.g., an integrase or a transposase) and a nucleic acid including an integration recognition site (e.g., a transposase recognition site).

Universal nucleotide sequence: A region of a sequence that is common to two or more nucleic acid molecules, where the molecules also have regions that differ from each other. A universal sequence that is present in different members of a collection of molecules can allow for the capture of several different nucleic acids using a population of universal capture nucleic acids (i.e., the adapter that has a sequence that is complementary to at least a portion of a primer). Similarly, a universal sequence that is present in different members of a collection of molecules can allow for the amplification or replication of several different nucleic acids using a population of universal sequencing binding sites (sequencing primer sequences).

Flow Cells and Methods of Making

In some of the examples disclosed herein, the flow cell includes: a substrate, which includes nano-depressions defined in a surface of the substrate and interstitial regions separating the nano-depressions; and a hydrophobic material layer i) having a surface that is at least substantially co-planar with the interstitial regions and ii) positioned to define a hydrophobic barrier around respective sub-sets of the nano-depressions. Different examples of the flow cells 10A-10I are shown in FIG. 1 through FIG. 9. Various features of the flow cells 10A-10I will be described in reference to FIG. 1 through FIG. 9 together, and then the methods for making each individual flow cell 10A-10I will be described in reference to the individual figure in which the flow cell 10A-10I is shown.

Each of the example flow cells 10A-10I includes a patterned substrate 12. The substrate 12 is generally rigid and is insoluble in an aqueous liquid. The substrate 12 may be a single layered or a multi-layered structure. Examples of suitable substrates 12 include epoxy siloxane, polyhedral oligomeric silsequioxanes (POSS) or derivatives thereof, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HaO_2$), inorganic glasses, or the like. Some examples of suitable plastics for the substrate 12 include acrylics, polystyrene, copolymers of styrene and other materials, polypropylene, polyethylene, polybutylene, polyurethanes, polytetrafluoroethylene (such as TEFLON® from The Chemours Co.), cyclic olefins/cyclo-olefin polymers (COP) (such as ZEONOR® from Zeon), polyimides, etc. The substrate 12 may also be glass or silicon or POSS, with a coating layer of tantalum oxide or another ceramic oxide at the surface. The substrate 12 may also be glass or silicon, with a coating layer of POSS at the surface.

The form of the substrate 12 may be a wafer, a panel, a rectangular sheet, a die, or any other suitable configuration. In an example, the substrate 12 may be a circular wafer or panel having a diameter ranging from about 2 mm to about 300 mm. As a more specific example, the substrate 12 is a wafer having a diameter ranging from about 200 mm to about 300 mm. In another example, the substrate 12 may be a rectangular sheet or panel having its largest dimension up to about 10 feet (~3 meters). As a specific example, the substrate 12 is a die having a width ranging from about 0.1 mm to about 10 mm. While example dimensions have been provided, it is to be understood that a substrate 12 with any suitable dimensions may be used.

Each of the example flow cells 10A-10I also includes the nano-depressions 14. In each of the examples, the nano-depressions 14 are defined in the patterned substrate 12. The nano-depressions 14 are considered to be "defined in" the substrate 12 because i) the substrate surface $S_{12}$ defines the interstitial regions 16 that separate the nano-depressions 14, ii) another substrate surface $S'_{12}$ defines a bottom surface of the nano-depressions 14, and iii) the substrate 12 also defines the walls of the nano-depressions 14.

Methods for generating the nano-depressions 14 will be described in more detail in reference to each of FIG. 1 through FIG. 9.

The nano-depressions 14 may be distributed across the substrate 12 in any suitable pattern or layout. Sub-sets 18A, 18B of the nano-depressions 14 may be separated by a hydrophobic barrier 20A-20I. The pattern of nano-depressions 14 in each sub-set 18A, 18B may be the same; or different patterns of nano-depressions 14 may be used in different sub-sets 18A, 18B. Many different patterns/layouts of the nano-depressions 14 may be envisaged, including regular, repeating, and non-regular patterns. In an example, the nano-depressions 14 are disposed in a hexagonal grid for close packing and improved density. Other layouts may include, for example, parallelogram layouts (i.e., rectangular, square, etc.), triangular layouts, circular layouts, and so forth.

Each nano-depression 14 may have any suitable shape (and corresponding 3-dimensional geometry), such as a circle, an oval, a polygon (e.g., triangle, quadrilateral, pentagon, etc.), etc.

The size of each nano-depression 14 may be characterized by its opening area, diameter, and/or length and width. While the term nano-depression 14 is used herein, it is to be understood that one or more of the dimensions of the depression 14 may be on the nano-scale (e.g., from about 1 nm up to, but not including, 1000 nm) or on the micro-scale (e.g., from about 1 μm up to, but not including, 1000 μm).

The area occupied by each depression opening can be selected so that a complex cannot enter the nano-depression 14. In an example, the area for each depression opening can be at least about $1 \times 10^{-3}$ µm², about $1 \times 10^{-2}$ µm², about 0.1 µm², or about 0.5 µm², or about 1 µm², or about 4 µm². The area occupied by each depression opening can be less than or between the values specified above.

In some instances, the diameter or length and width of each nano-depression 14 can be at least about 1 nm, 50 nm, about 100 nm, about 500 nm, up to about 2 µm. An example of the depression diameter ranges from about 1 nm to about 500 nm. Another example of the depression diameter ranges from about 300 nm to about 1 µm.

The nano-depression 14 may also have a depth. As examples, the depth of each depression 16 can be at least about 10 nm, at least about 50 nm, at least about 1 µm, about 10 µm, about 50 µm, or more. In some examples, the depth is about 0.4 µm. It is to be understood that the depth of each nano-depression 14 can be greater than, less than or between the values specified above.

Adjacent nano-depressions 14 are separated by the interstitial regions 16 within a given sub-set 18A, 18B. The sub-sets 18A, 18B are separated by an example of the hydrophobic barrier 20A-20I. The average depression pitch represents the spacing from the center of one nano-depression 14 to the center of an adjacent nano-depression 14 (center-to-center spacing) or from the edge of one nano-depression 14 to the edge of an adjacent nano-depression 14 (edge-to-edge spacing). The layout or pattern of the nano-depressions 14 can be regular, such that the coefficient of variation around the average pitch is small, or the layout or pattern can be non-regular in which case the coefficient of variation can be relatively large. In either case, the average pitch can be, for example, at least about 10 nm, or at least about 0.1 µm, or at least about 0.5 µm, or more, depending upon the configuration of the hydrophobic barrier 20A, 20B, 20C, 20D. Alternatively or additionally, the average pitch can be, for example, at most about 0.5 µm, or at most about 0.1 µm, or less. The average pitch for a particular pattern of nano-depressions 14 can be between one of the lower values and one of the upper values selected from the ranges above.

The configuration of the hydrophobic barrier 20A, 20B, 20C, 20D is different in each of the flow cells 10A, 10B, 10C, 10D. These configurations will be described individually in reference to FIG. 1, FIG. 2, FIG. 3 and FIG. 4. The configuration of the hydrophobic barrier 20E-20I (shown in FIG. 5 through FIG. 9) is similar to the hydrophobic barrier 20B shown in FIG. 2 (see 2(*vii*)), although it is to be understood that the methods described in FIG. 5 through FIG. 9 could be used to form the hydrophobic barrier 20A shown in FIG. 1 (see 1(*vii*)) as well. One common characteristic of the configurations is that the hydrophobic barrier 20A-20I defines a perimeter around each sub-set of nano-depressions 14. The portion of the flow cell 10A-10I within the perimeter (e.g., the portion where the sub-sets of nano-depressions 14 are located) may be referred to as a chamber 24.

The size of each chamber 24 may be characterized by its area, diameter, and/or length and width. Because the chamber 24 is defined by the at least substantially co-planar hydrophobic barrier 20A-20I, it is to be understood that the chamber 24 may not have a depth, and when it does have a depth, it is less than about 2 µm.

In an example, the area of each chamber 24 can be at least about 1 µm², about 10 µm², about 100 µm², or more. The area occupied by each chamber 24 can be greater than or between the values specified above.

In some instances, the diameter or length and width of each chamber 24 can be at least about 1 µm, about 10 µm, about 20 µm, about 30 µm, about 40 µm, about 50 µm, about 100 µm, or more. An example of the chamber 24 diameter ranges from about 1 µm to about 1000 µm. Another example of the chamber diameter ranges from about 10 µm to about 50 µm. When the chamber 24 has a length and width, it is to be understood that the length and width may be the same or different.

The chamber 24 may or may not have a depth. This depth depends upon whether the hydrophobic material layer 22, and thus the hydrophobic barrier 20, extends outward in the Z-direction beyond the surface of the interstitial regions 16. In any of the examples disclosed herein, the depth is not more than 2 µm.

Each example of the hydrophobic barrier 20A-20I also includes a hydrophobic material or hydrophobic material layer 22. As is described in more detail with reference to the various methods, a hydrophobic material may be applied to form the hydrophobic material layer 22. In any of the examples disclosed herein, the hydrophobic material or hydrophobic material layer 22 is selected from the group consisting of a fluorinated polymer, a perfluorinated polymer, a silicon polymer, and a mixture thereof. As examples, the hydrophobic material or hydrophobic material layer 22 may include an amorphous fluoropolymer (commercially available examples of which include those in the CYTOP® series from AGC Chemicals, which have one of the following terminal functional groups: A type: —COOH, M type: —CONH—Si(OR)$_n$, or S type: —CF$_3$), a polytetrafluoroethylene (a commercially available example of which is TEFLON® from Chemours), parylen, a fluorinated hydrocarbon, a fluoroacrylic copolymer (a commercially available example of which includes as FLUOROPEL® from Cytonix), a fluorosilane (e.g., Trichloro(1H,1H,2H,2H-perfluorooctyl)silane (PFOTS), perfluorodecyltrichlorosilane (FDTS), etc.), a plasma-deposited fluorocarbon, polydimethylsiloxane, other siloxanes, or a mixture thereof. As another example, the hydrophobic material or hydrophobic material layer 22 may include a hydrophobic hydrocarbon, such as 1-heptadecyne.

Referring now to FIG. 1, an example of the method for forming the hydrophobic barrier 20A is schematically depicted. In this example method, a patterned substrate 12 is used (see FIG. 1(*ii*)), or is generated from a non-patterned substrate 12' as part of the method (see FIG. 1(*i*) and FIG. 1(*ii*)). In FIG. 1(*ii*), the patterned substrate 12 includes the nano-depressions 14 defined in the substrate surface $S_{12}$, the interstitial regions 16 separating the nano-depressions 14, and a barrier interstitial 26 around the respective sub-sets 18A, 18B of the nano-depressions 14 and the interstitial regions 16.

The barrier interstitial 26 is the portion of the substrate surface $S_{12}$ that supports the hydrophobic barrier 20A that is ultimately formed. In other words, during the method, the hydrophobic barrier 20A is formed on the barrier interstitial 26. As such, the barrier interstitial 26 has the shape/configuration and X- and Y-dimensions that are desired for the hydrophobic barrier 20, and defines a perimeter (see, e.g., FIG. 11) around each of the sub-sets 18A, 18B of the nano-depressions 14.

The non-patterned substrate 12' may be patterned to form the various features 14, 16, 26. Patterning may involve etching, nanoimprint lithography (NIL), or combinations thereof, depending, in part, upon the type of substrate that is used. Other patterning techniques may also be used, such as photolithography, stamping techniques, embossing techniques, molding techniques, microetching techniques, etc.

This example of the method includes applying a hydrophobic material on the patterned substrate 12 (FIG. 1(*iii*)), thereby forming a hydrophobic material layer 22 i) in the nano-depressions 14 and ii) on the interstitial regions 16, 26, wherein the hydrophobic material layer 22 on the interstitial regions 16, 26 has a thickness less than about 2 µm. Any example of the hydrophobic materials disclosed herein may be used. Any suitable technique may be used that is capable of applying the hydrophobic material as a thin film. Example deposition techniques include spin coating, chemical vapor deposition, dip coating, dunk coating, spray coating, puddle dispensing, ultrasonic spray coating, doctor blade coating, aerosol printing, screen printing, microcontact printing, etc.

As shown at FIG. 1(*iii*) and FIG. 1(*iv*), this example of the method also includes applying a mask material 28 on a first portion 30 of the hydrophobic material layer 22 to define a pattern of the hydrophobic barrier 20A around respective sub-sets 18A, 18B of the nano-depressions 14 and the interstitial regions 16, whereby a second portion 32 of the hydrophobic material layer 22 is exposed at the respective sub-sets 18A, 18B.

In some instances, the hydrophobic material layer 22 may be exposed to an oxygen plasma treatment before depositing the mask material 28.

The mask material 28 may be any suitable material that exhibits a change in solubility when exposed to a particular external stimulus. In an example, the mask material 28 is a photoresist. Photoresist materials change solubility with respect to a developer solution when exposed to certain wavelengths of light. The photoresist may be a positive photoresist material (exposed region becomes soluble) or a negative photoresist material (exposed region becomes insoluble). Examples of suitable positive photoresists include the MICROPOS IT® S1800 series or the AZ® 1500 series, both of which are available from MicroChemicals. An example of suitable negative photoresist includes the epoxy-based SU-8 photoresist (available from MicroChemicals). In other examples, the mask material 28 may include a bi-layer resist, wherein one layer (e.g., deposited directly on the substrate 12) is a lift-off layer and another layer (e.g., deposited on the lift-off layer) is an imaging layer.

As shown in FIG. 1(*iii*) and FIG. 1(*iv*), the selective application of the mask material 28 may involve depositing the material 28 on the hydrophobic material layer 22 (FIG. 1(*iii*)), and patterning the material 28, e.g., by photolithography, so that the portion(s) 30 of the hydrophobic material layer 22 remain covered and the portion(s) 32 of the hydrophobic material layer 22 are exposed (FIG. 1(*iv*)). In this example, the portion(s) 30 of the hydrophobic material layer 22 that remain covered after patterning are positioned on the barrier interstitial 26, and the portion(s) 32 of the hydrophobic material layer 22 that are exposed after patterning are positioned in the nano-depressions 14 and on the interstitial regions 16 of each sub-set 18A, 18B. When the mask material 28 is a positive photoresist material, the regions of the mask material 28 directly adjacent to the portion(s) 32 of the hydrophobic material layer 22 may be exposed to light of a suitable wavelength so that they become soluble and can be removed using a suitable developer solution. When the mask material 28 is a negative photoresist material, the regions of the mask material 28 directly adjacent to the portion(s) 30 of the hydrophobic material layer 22 may be exposed to light of a suitable wavelength so that they become insoluble. The portions of the mask material 28 not exposed to light remain soluble and can be removed using a suitable developer solution.

This example of the method also includes removing the second portion(s) 32 of the hydrophobic material layer 22 (as shown at FIG. 1(*v*)), thereby exposing the respective sub-sets 18A, 18B of the nano-depressions 14 and the interstitial regions 16. Removal of the second portion(s) 32 of the hydrophobic material layer 22 may involve etching. In an example, plasma etching with air or oxygen ($O_2$) gas may be used. In another example, dry etching with oxygen ($O_2$) gas may be used. The mask material 28 and substrate 12 may have different etch rates than the hydrophobic material layer 22, so that the mask material 28 is not susceptible to the etching process, and the underlying substrate 12 acts as an etch stop once the second portion(s) 32 of the hydrophobic material layer 22 are removed.

As shown at FIG. 1(*vi*), this example method also involves attaching a gel material 34 to the nano-depressions 14 of the respective sub-sets 18A, 18B. In some examples, a lift-off gel patterning method may be used. In these examples, attaching the gel material 34 involves silanizing the nano-depressions 14 and interstitial regions 16 of the respective sub-sets 18A, 18B and depositing the gel material 34 on the nano-depressions 14 and interstitial regions 16 of the respective sub-sets 18A, 18B and on the mask material 28.

Silanizing may include depositing a silane or silane derivative. The silane or silane derivative may include functional groups that are capable of forming covalent bonds with the gel material 34. Examples of the functional groups in the silane include vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbine, isocyanate or maleimide, or optionally substituted variants or combinations thereof. Examples of the silane or silane derivative including an amino functional group include (3-aminopropyl)triethyoxysilane (APTES) or (3-aminopropyl)trimethoxy silane APTMS. One example of a suitable derivative is a norbornene derivatized silane, such as [(5-bicyclo[2.2.1]hept-2-enyl)ethyl]trimethoxysilane. The silane may be deposited via chemical vapor deposition (CVD) or another suitable deposition technique. The silane or silane derivative may be applied to the mask material 28, but may or may not attach to the mask material 28.

While silanization is described throughout this disclosure, it is to be understood that other activation processes may be used instead of silanization. For example, activation may involve plasma ashing to generate surface-activating agent(s) (e.g., —OH groups) that can adhere to the gel material 34.

The gel material 34 may then be applied. An example of a polymer that may be used as the material 34 includes an acrylamide copolymer, such as poly(N-(5-azidoacetamidylpentyl)acrylamide-co-acrylamide, PAZAM. PAZAM and some other forms of the acrylamide copolymer are represented by the following structure (I)

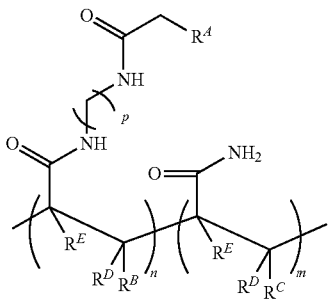

wherein:
- $R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
- $R^B$ is H or optionally substituted alkyl;
- $R^C$, $R^D$, and $R^E$ are each independently selected from the group consisting of H and optionally substituted alkyl;
- each of the —$(CH_2)_p$— can be optionally substituted;
- p is an integer in the range of 1 to 50;
- n is an integer in the range of 1 to 50,000; and
- m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

In some examples, PAZAM is a linear polymer. In some other examples, PAZAM is a lightly cross-linked polymer.

In other examples, the polymer that may be used to form the layer 26 may be a variation of the structure (I). In one example, the acrylamide unit may be replaced with N,N-dimethylacrylamide

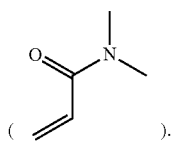

In this example, the acrylamide unit in structure (I) may be replaced with

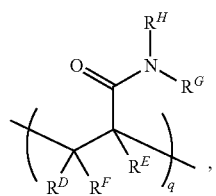

where $R^D$, $R^E$, and $R^F$ are each H or a C1-C6 alkyl, and $R^G$ and $R^H$ are each a C1-C6 alkyl group (instead of H as is the case with the acrylamide). In this example, q may be an integer in the range of 1 to 100,000. In another example, N,N-dimethylacrylamide may be used in addition to the acrylamide unit. In this example, structure (I) may include

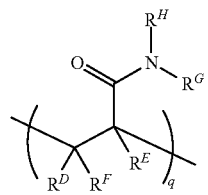

in addition to the recurring "n" and "m" features, where $R^D$, $R^E$, and $R^F$ are each H or a C1-C6 alkyl, and $R^G$ and $R^H$ are each a C1-C6 alkyl group. In this example, q may be an integer in the range of 1 to 100,000.

It is to be understood that other polymers or molecules may be used as the gel material 34, as long as they are functionalized to interact with the siliane or silane derivative or other activated surface groups, and subsequently applied primers 36. Other examples of suitable polymers for the gel material 34 include those polymers having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photocycloaddition reactions. Still other examples of suitable polymers for the gel material 34 include mixed copolymers of acrylamides and acrylates.

The gel material 34 may be applied using spin coating, or dipping or dip coating, or another suitable technique. The gel material 34 may also be exposed to a curing process. The conditions of curing will depend on the type of gel material 34 that is used. In an example, curing may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The gel material 34 may be covalently attached to the layer of silane or silane derivative.

Some examples of the method further include removing the gel material 34 from the mask material 28 and from the interstitial regions 16. These examples of the method also include removing the mask material 28 from the first portion(s) 30 of the hydrophobic material layer 22 to reveal the hydrophobic barrier 20A (FIG. 1(vii)).

In some examples, the portions of silane/silane derivative layer and the gel material 34 that directly overly the mask material 28 may be removed via washing. In some instances, the silane or silane derivative does not attach (e.g., via bonding) to the mask material 28, and thus the gel material 34 is also not attached to the mask material 28. As such, these portions of the silane/silane derivative layer and the gel material 34 can be readily washed away from the mask material 28 using water. It is to be understood that the remainder of the gel material 34 is attached to the layer of silane or silane derivative, which does attach to the substrate surfaces $S_{12}$ (e.g., at the interstitial regions 16) and $S'_{12}$ (e.g., in the nano-depressions 14), and the gel material 34 that thus directly overlies these features 14, 16 are not removed via washing.

Because the remainder of the gel material 34 is immobilized at the interstitial regions 16 and in the nano-depressions 14, the mask material 28 may then be removed or lifted off without deleteriously affecting the gel material 34. The mask material 28 may be removed by various reagents, depending on the type of mask material 28 that is used. Some suitable removers include 1-methyl-2-pyrrolidone, dimethyl sulfoxide, or those available from MicroChemicals, an example of which is sold under the tradename AZ® 100 Remover (capable of removing the AZ® photoresists). Removal of the mask material 28 exposes the underlying portion(s) 30 of the hydrophobic material layer 22, and reveals the hydrophobic barrier 20A.

In other examples, the portions of silane/silane derivative layer and the gel material 34 that directly overly the mask material 28 may be removed simultaneously with the mask material 28. In these examples, a lift-off method may be used to remove the mask material 28 and any of the silane/silane derivative layer and the gel material 34 thereon.

The remainder of the gel material 34 may be exposed to polishing. Polishing can remove the gel material 34, and in some instances, at least part of the silane or silane derivative, from the interstitial regions 16 without deleteriously affecting the gel material 34 in the nano-depressions 14 and without deleteriously affecting the hydrophobic barrier 20A. The polishing process may be performed with a gentle chemical slurry (including, e.g., an abrasive, a buffer, a chelating agent, a surfactant, and/or a dispersant). Alternatively, polishing may be performed with a solution that does not include the abrasive particles. The chemical slurry may be used in a chemical mechanical polishing system to polish the surface of the interstitial regions 16. The polishing head(s)/pad(s) or other polishing tool(s) is/are capable of polishing the gel material 34 from the interstitial regions 16 while leaving the material 34 in the depressions 14.

The hydrophobic barrier 20A is also capable of remaining intact during and after polishing. In this example, hydrophobic barrier 20A is formed on the barrier interstitial 26, and thus does extend outward in the Z-direction slightly above the interstitial regions 16. During the application of the hydrophobic material to form the hydrophobic material layer 22, the thickness is controlled so that the portion 30 formed on the interstitial region 26 is less than about 2 μm. Because this portion 30 forms the hydrophobic barrier 20A, the thickness $T_{20A}$ of the hydrophobic barrier 20A is also less than about 2 μm.

The portion of the flow cell 10A shown in FIG. 1(vii) also has primers 36 grafted to the gel material 34 in the depressions 14. A grafting process may be performed to graft the primers 36. In an example, grafting may involve flow through deposition (e.g., using a temporarily bound lid), dunk coating, spray coating, puddle dispensing, or by another suitable method that will attach the primer(s) 36 to the gel material 34 in the depressions 13. Each of these example techniques may utilize a primer solution or mixture, which may include the primer(s), water, a buffer, and a catalyst. With any of the grafting methods, the primers 36 react with reactive groups of the gel material 34 in the depressions 14 and have no affinity for the interstitial regions 16 or the hydrophobic barrier 20A.

In an example, the primers 36 can be immobilized to the gel material 34 by single point covalent attachment at or near the 5' end of the primers 36. This attachment leaves i) the adapter-specific portion of the primers 36 free to anneal to its cognate sequencing-ready nucleic acid fragment and ii) the 3' hydroxyl group free for primer extension. Any suitable covalent attachment may be used for this purpose. Examples of terminated primers that may be used include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. In some examples, two different primers 36 are used. Specific examples of suitable primers 36 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, and other instrument platforms.

Figure 2:
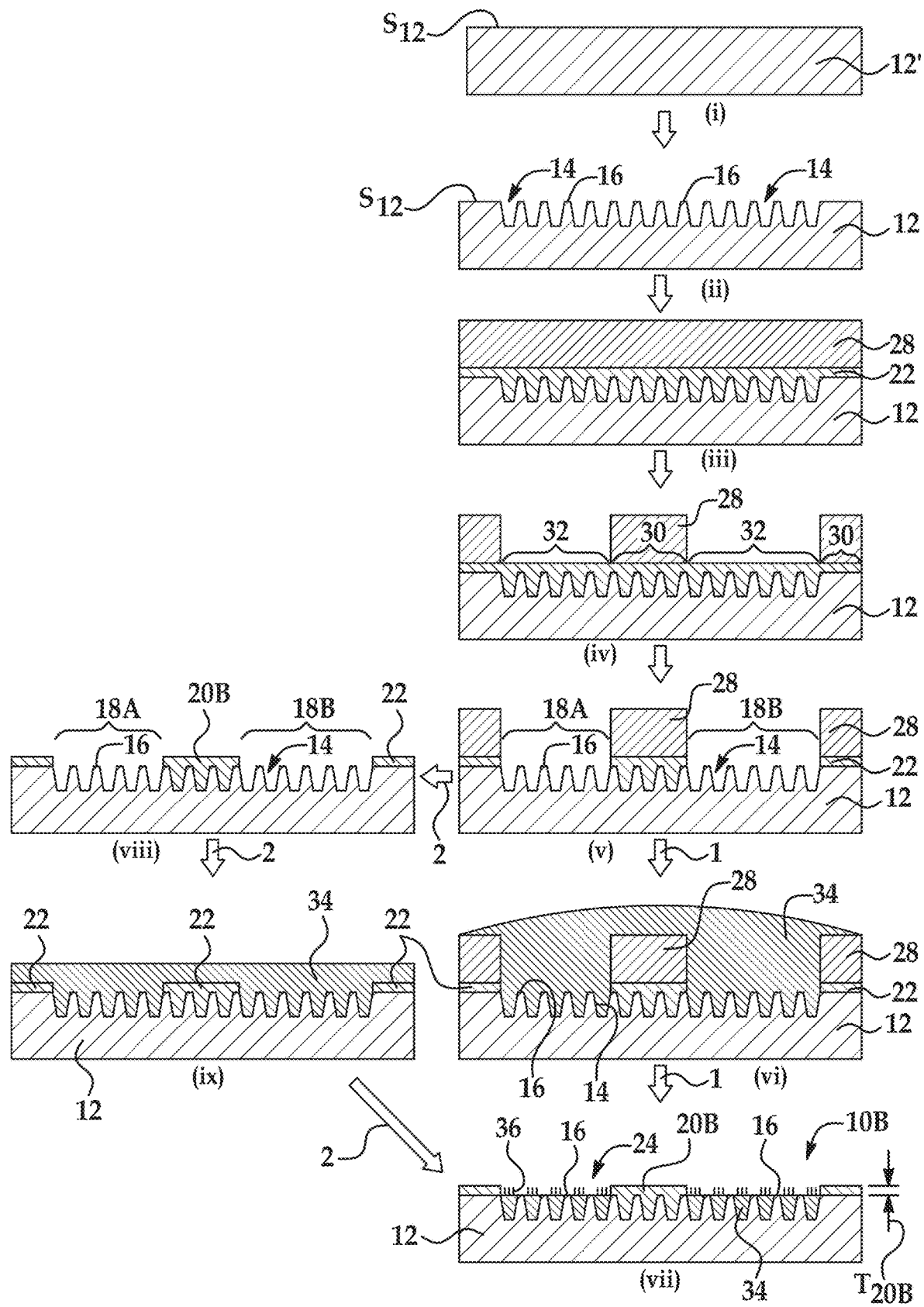
FIG. 2 is a schematic flow diagram including (i) through (ix) illustrating another example of the methods disclosed herein to form another example of the flow cell disclosed herein.

Referring now to FIG. 2, two examples of the method for forming the hydrophobic barrier 20B (FIG. 2(vii)) are schematically depicted. In these example methods, a patterned substrate 12 is used (FIG. 2(ii)), or is generated from a non-patterned substrate 12' as part of the method (FIG. 2(i) through FIG. 2(ii)). The patterned substrate 12 includes the nano-depressions 14 defined in the substrate surface $S_{12}$ and the interstitial regions 16 separating the nano-depressions 14 (FIG. 2(ii))

The non-patterned substrate 12' may be patterned to form the various features 14, 16. Patterning may involve using any of the examples set forth herein in reference to FIG. 1.

These examples of the method include applying a hydrophobic material on the patterned substrate 12 ((FIG. 2(iii)), thereby forming a hydrophobic material layer 22 i) in the nano-depressions 14 and ii) on the interstitial regions 16, wherein the hydrophobic material layer 22 on the interstitial regions 16 has a thickness less than about 2 μm. Any example of the hydrophobic materials disclosed herein may be used, and any suitable technique to applying the hydrophobic material may be used.

These examples of the method also include applying a mask material 28 on a first portion 30 of the hydrophobic material layer 22 to define a pattern of the hydrophobic barrier 20B around respective sub-sets 18A, 18B of the nano-depressions 14 and the interstitial regions 16, whereby a second portion 32 of the hydrophobic material layer 22 is exposed at the respective sub-sets 18A, 18B.

Any example of the mask material 28 disclosed herein may be used.

As shown in FIG. 2, the selective application of the mask material 28 may involve depositing the material 28 on the hydrophobic material layer 22 (FIG. 2(iii)), and patterning the material 28, e.g., by photolithography, so that the portion (s) 30 of the hydrophobic material layer 22 remain covered and the portion(s) 32 of the hydrophobic material layer 22 are exposed (FIG. 2(iv)). In these examples, patterning of the mask material 28 defines the sub-sets 18A, 18B. In particular, the portion(s) 30 of the hydrophobic material layer 22 that remain covered by the mask material 28 will define the hydrophobic barrier 20B. As such, in this example, the portions 30 have the shape/configuration and X- and Y-dimensions that are desired for the hydrophobic barrier 20B, and define the perimeters around each of the sub-sets 18A, 18B of the nano-depressions 14. Patterning of the mask material 28 may be performed as described in reference to FIG. 1.

As shown at FIG. 2(iv), this example of the method also includes removing the second portion(s) 32 of the hydrophobic material layer 22, thereby exposing the respective sub-sets 18A, 18B of the nano-depressions 14 and the interstitial regions 16. Removal of the second portion(s) 32 of the hydrophobic material layer 22 may involve etching. In examples, plasma etching with air or oxygen ($O_2$) gas may be used, or dry etching with oxygen ($O_2$) gas may be used. The mask material 28 and substrate 12 may have different etch rates than the hydrophobic material layer 22, so that the mask material 28 is not susceptible to the etching process, and the underlying substrate 12 acts as an etch stop once the second portion(s) 32 of the hydrophobic material layer 22 are removed.

Unlike the method shown in FIG. 1, some of the nano-depressions 14 remain filled with the hydrophobic material layer 22 because these nano-depressions 14 are covered by the portion(s) 30 of the mask material 28. This is shown in FIG. 2(iv).

In one example of the methods shown in FIG. 2 (including 2(v)-2(vii) and denoted by the arrows labeled "1"), a gel material 34 is attached to the nano-depressions 14 of the respective sub-sets 18A, 18B (FIG. 2(vi)). The lift-off gel patterning method described in reference to FIG. 1 may be used in this example method. As an example, attaching the gel material 34 involves silanizing the nano-depressions 14 and interstitial regions 16 of the respective sub-sets 18A, 18B and depositing the gel material 34 on the nano-depressions 14 and interstitial regions 16 of the respective sub-sets 18A, 18B and on the remaining mask material 28.

Some examples of this method further includes removing the gel material 34 from the mask material 28 and from the interstitial regions 16; and removing the mask material 28 from the first portion(s) 30 of the hydrophobic material layer 22 to reveal the hydrophobic barrier 20B. Other examples of this method include removing the mask material 28 and any gel material 34 thereon simultaneously.

In some examples, the portions of silane/silane derivative layer and the gel material 34 that directly overly the mask material 28 may be removed via washing. Because the remainder of the gel material 34 is immobilized at the interstitial regions 16 and in the nano-depressions 14 of the sub-sets 18A, 18B, the mask material 28 may then be removed or lifted off without deleteriously affecting the gel material 34. The mask material 28 may be removed using any suitable reagent as described herein. Removal of the mask material 28 exposes the underlying portion(s) 30 of the hydrophobic material layer 22, and reveals the hydrophobic barrier 20B. In other examples, the mask material 28 and any silane/silane derivative layer and gel material 34 that directly overly the mask material 28 may be removed simultaneously.

The remainder of the gel material 34 may be exposed to polishing. Polishing can remove the gel material 34, and in some instances, at least part of the silane or silane derivative, from the interstitial regions 16 without deleteriously affecting the gel material 34 in the nano-depressions 14 and without deleteriously affecting the hydrophobic barrier 20B (FIG. 2(vii)). Polishing may be performed as described herein in reference to FIG. 1.

In another example of the methods shown in FIG. 2 (including FIG. 2(viii) through FIG. 2(ix) and FIG. 2(vii)) and denoted by the arrows labeled "2"), the mask material 28 is removed prior to the application of the gel material 34. The mask material 28 may be removed as described in reference to FIG. 1. Removal of the mask material 28 from the first portion(s) 30 of the hydrophobic material layer 22 reveals the hydrophobic barrier 20B (see FIG. 2(viii)).

In this example of the method shown in FIG. 2(ix), the gel material 34 is attached to the nano-depressions 14 of the respective sub-sets 18A, 18B. As an example, attaching the gel material 34 involves silanizing the nano-depressions 14 and interstitial regions 16 of the respective sub-sets 18A, 18B and depositing the gel material 34 on the nano-depressions 14 and interstitial regions 16 of the respective sub-sets 18A, 18B and on the hydrophobic barrier 20B. Examples of this method further include removing the gel material 34 from the hydrophobic barrier 20B and from the interstitial regions 16. Gel material 34 removal may involve polishing. This process leaves the gel material 34 intact in the nano-depressions 14 and also leaved the hydrophobic barrier 20B intact, as shown in FIG. 2(vii).

In both of the examples shown in FIG. 2, the hydrophobic barrier 20B is capable of remaining intact after polishing. In these examples, hydrophobic barrier 20B is formed in some of the depressions 14 and on some of the interstitial regions 16 that are positioned between respective sub-sets 18A, 18B. As depicted in FIG. 2(vii), a portion of the hydrophobic barrier 20B does extend outward in the Z-direction slightly above the interstitial regions 16. During the application of the hydrophobic material to form the hydrophobic material layer 22, the thickness is controlled so that the portion 30 formed on the interstitial regions 16 is less than about 2 μm. Because this portion 30 forms the hydrophobic barrier 20B, the thickness $T_{20B}$ is also less than about 2 μm. In this example, the total thickness varies across the hydrophobic barrier 20B (e.g., it is thicker in the depressions 14 than on the interstitial regions 16), but the thickness $T_{20B}$ of the portion of the hydrophobic barrier 20B that extends above the interstitial regions 16 is consistently less than about 2 μm.

The portion of the flow cell 10B shown in FIG. 2(vii) also has primers 36 grafted to the gel material 34 in the depressions 14 of the sub-sets 18A, 18B. Any of the primers 36 and the grafting processes described in reference to FIG. 1 may be used.

Figure 3:
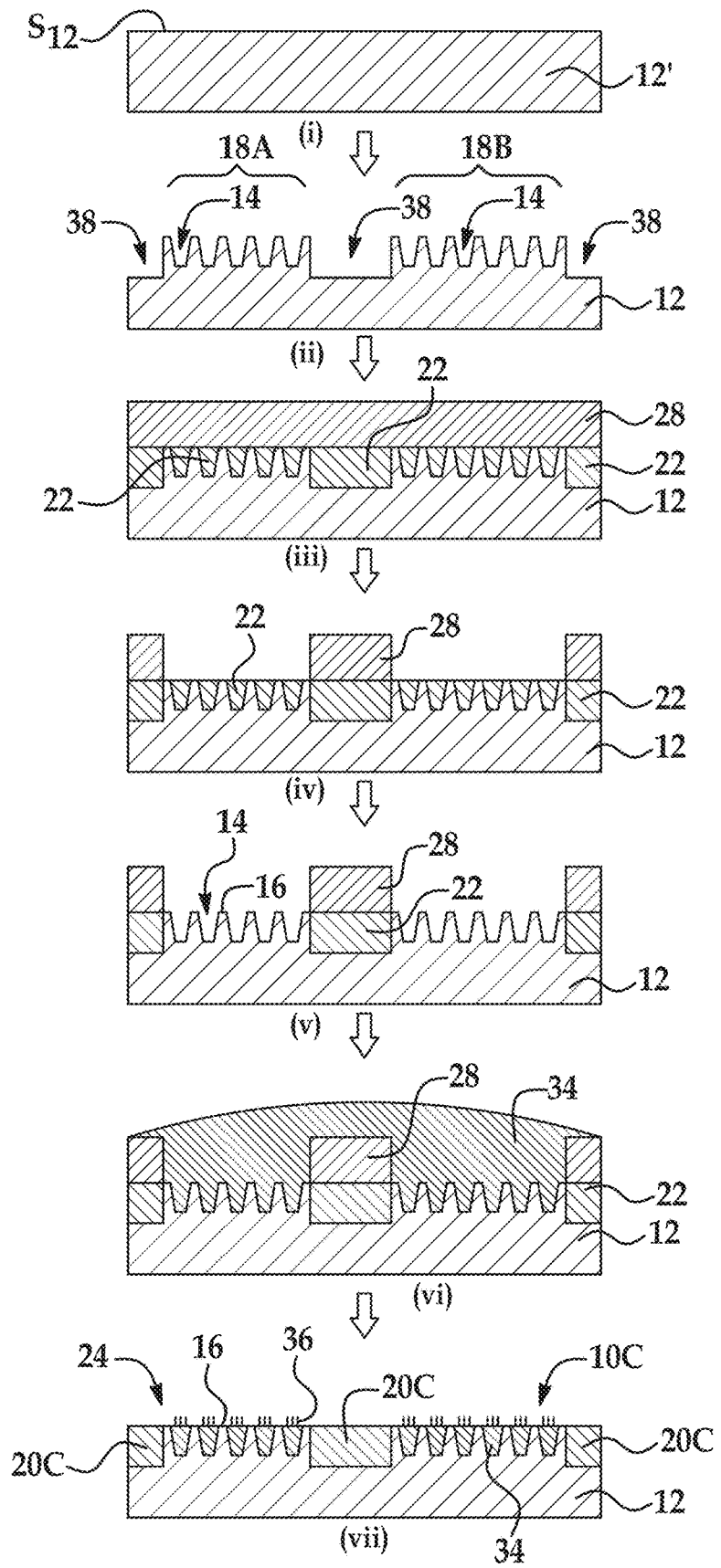
FIG. 3 is a schematic flow diagram including (i) through (vii) illustrating still another example of the methods disclosed herein to form still another example of the flow cell disclosed herein.

Referring now to FIG. 3, an example of the method for forming the hydrophobic barrier 20C is schematically depicted. In this example method, a patterned substrate 12 is used (FIG. 3(ii)), or is generated from a non-patterned substrate 12' as part of the method (FIG. 3(i) through FIG. 3(ii)).

As shown in FIG. 3(ii), the patterned substrate 12 includes sub-sets 18A, 18B of nano-depressions 14 defined in the substrate surface $S_{12}$, the interstitial regions 16 separating the nano-depressions 14, and a barrier depression 38 defined in the surface $S_{12}$ of the patterned substrate 12 around each of the sub-sets 18A, 18B.

The barrier depression 38 is defined in a portion of the substrate surface $S_{12}$ and ultimately supports the hydrophobic barrier 20C that is formed. In other words, during the method, the hydrophobic barrier 20C is formed in the barrier depression 38. As such, the barrier depression 38 has the shape/configuration and X- and Y-dimensions that are desired for the hydrophobic barrier 20C, and defines a perimeter (see, e.g., FIG. 11) around each of the sub-sets 18A, 18B of the nano-depressions 14.

The non-patterned substrate 12' may be patterned to form the various features 14, 16, 38. Patterning may involve any of the examples set forth herein in reference to FIG. 1.

This example of the method includes applying a hydrophobic material on the patterned substrate 12, thereby forming a hydrophobic material layer 22 i) in the barrier depression 38 and ii) in the nano-depressions 14 (see FIG. 3(iii)). In this example, it is desirable to fill or underfill the depressions 14, 38 so that the hydrophobic material does not extend onto the interstitial regions 16. In this example, the hydrophobic material layer 22 may be co-planar with the interstitial regions 16. Any example of the hydrophobic materials disclosed herein may be used, and any suitable technique to selectively apply the hydrophobic material may be used. In a specific example, the hydrophobic material is one of the polymers in the CYTOP® series.

This example of the method also includes applying a mask material 28 on the hydrophobic material layer 22 in the barrier depression 38, as shown in FIG. 3(*iii*).

Any example of the mask material 28 disclosed herein may be used.

As shown in FIG. 3 (at (iii) and (iv)), the selective application of the mask material 28 may involve depositing the material 28 on the hydrophobic material layer 22 (that is in the nano-depressions 14 and the barrier depression 38) (FIG. 3(*iii*)), and patterning the material 28, e.g., by photolithography, so that the hydrophobic material layer 22 in the barrier depression 38 remains covered and the hydrophobic material layer 22 in each of the nano-depressions 22 is exposed (FIG. 3(*iv*)). Patterning of the mask material 28 may be performed as described in reference to FIG. 1.

This example of the method also includes removing the hydrophobic material layer 22 from the nano-depressions 14, as shown in FIG. 3(*v*). This removal process exposes the nano-depressions 14. Removal of the hydrophobic material layer 22 from the nano-depressions 14 may involve etching. In examples, plasma etching with air or oxygen ($O_2$) gas may be used, or dry etching with oxygen ($O_2$) gas may be used. The mask material 28 and substrate 12 may have different etch rates than the hydrophobic material layer 22, so that the mask material 28 is not susceptible to the etching process, and the underlying substrate 12 acts as an etch stop once the hydrophobic material layer 22 is removed from the nano-depressions 14.

This example method also involves attaching a gel material 34 to the nano-depressions 14 of the respective sub-sets 18A, 18B, as shown in FIG. 3(*vi*). The lift-off gel patterning method described in reference to FIG. 1 may be used in this example method. As an example, attaching the gel material 34 involves silanizing the nano-depressions 14 and interstitial regions 16 of the respective sub-sets 18A, 18B, and depositing the gel material 34 on the nano-depressions 14 and interstitial regions 16 of the respective sub-sets 18A, 18B and on the remaining mask material 28.

Some examples of the method further include removing the gel material 34 from the mask material 28 and from the interstitial regions 16; and removing the mask material 28 from the hydrophobic material layer 22 in the barrier depression 38 to reveal the hydrophobic barrier 20C. Other examples of the method include removing the mask material 28 and any gel material 34 thereon simultaneously. FIG. 3(*vii*) shows the flow cell 10C after the materials 28 and 34 are removed.

In some examples, the portions of silane/silane derivative layer and the gel material 34 that directly overly the mask material 28 may be removed via washing. Because the remainder of the gel material 34 is immobilized at the interstitial regions 16 and in the nano-depressions 14 of the sub-sets 18A, 18B, the mask material 28 may then be removed or lifted off without deleteriously affecting the gel material 34. The mask material 28 may be removed using any suitable reagent as described herein. Removal of the mask material 28 exposes the underlying portion(s) of the hydrophobic material layer 22 in the barrier depression 38, and reveals the hydrophobic barrier 20B (FIG. 3(*vii*)). In other examples, the mask material 28 and any silane/silane derivative layer and gel material 34 that directly overly the mask material 28 may be removed simultaneously.

The remainder of the gel material 34 may then be exposed to polishing. Polishing can remove the gel material 34, and in some instances, at least part of the silane or silane derivative, from the interstitial regions 16 without deleteriously affecting the gel material 34 in the nano-depressions 14 and without deleteriously affecting the hydrophobic barrier 20C. Polishing may be performed as described herein in reference to FIG. 1.

The hydrophobic barrier 20C is capable of remaining intact after polishing. In this example, hydrophobic barrier 20C is formed in the barrier depression 38. As depicted in FIG. 3(*vii*), a surface $S_{20C}$ of the hydrophobic barrier 20C does not extend outward in the Z-direction above the interstitial regions 16, and thus the hydrophobic barrier 20C is co-planar with the interstitial regions 16. In this example, the thickness of the hydrophobic barrier 20C corresponds with the depth of the barrier depression 38, and no portion of the thickness extends beyond the interstitial regions 16.

The portion of the flow cell 10C shown in FIG. 3(*vii*) also has primers 36 grafted to the gel material 34 in the depressions 14 of the sub-sets 18A, 18B. Any of the primers 36 and the grafting processes described in reference to FIG. 1 may be used.

Figure 4:
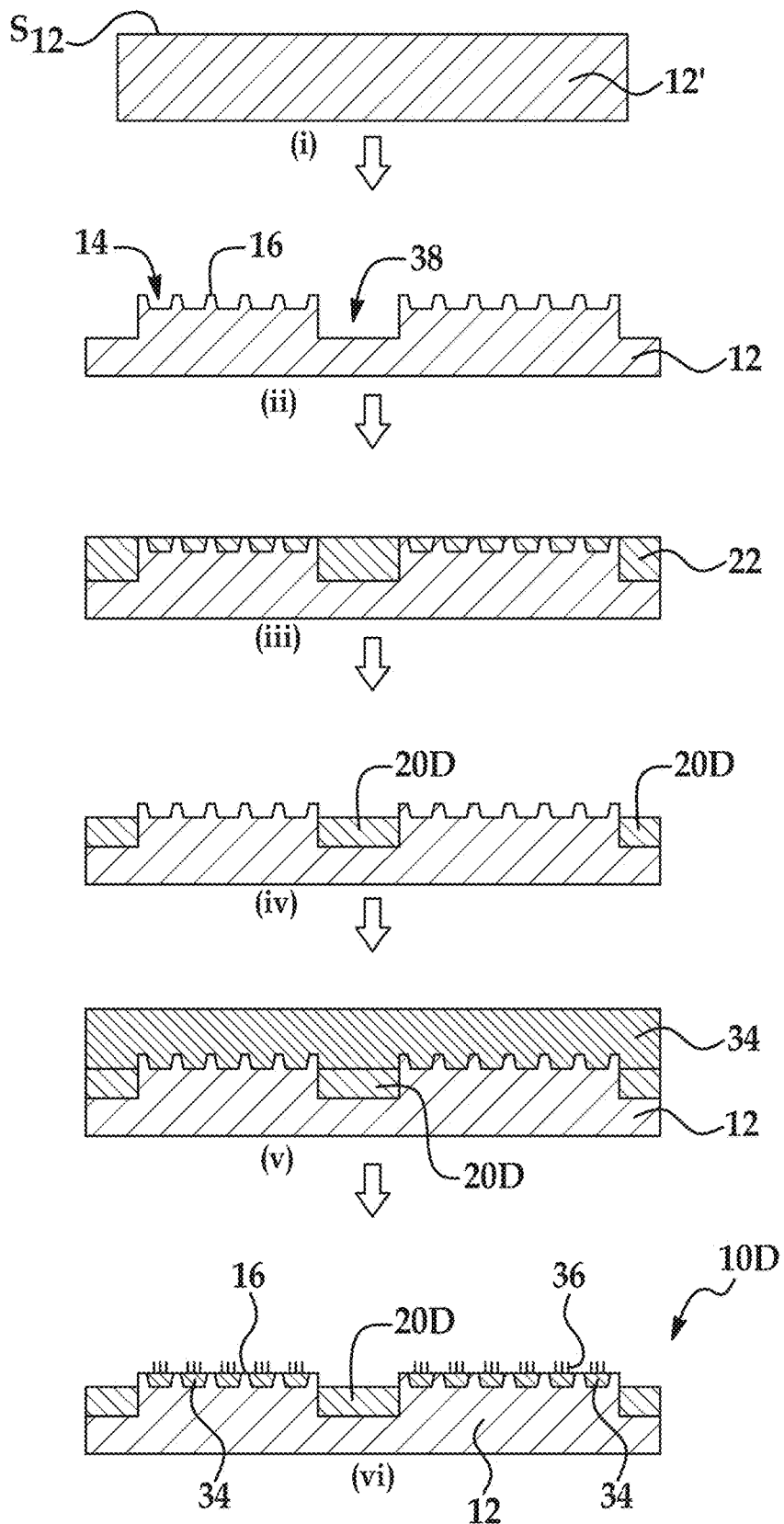
FIG. 4 is a schematic flow diagram including (i) through (vi) illustrating yet another example of the methods disclosed herein to form yet another example of the flow cell disclosed herein.

Referring now to FIG. 4, an example of the method for forming the hydrophobic barrier 20D is schematically depicted. In this example method, a patterned substrate 12 is used (FIG. 4(*ii*)), or is generated from a non-patterned substrate 12' as part of the method (FIG. 4(*i*) through FIG. 4(*ii*)).

The patterned substrate 12 includes sub-sets 18A, 18B of nano-depressions 14 defined in the substrate surface $S_{12}$, the interstitial regions 16 separating the nano-depressions 14, and the barrier depression 38 defined in the surface $S_{12}$ of the patterned substrate 12 around each of the sub-sets 18A, 18B. The depth of the barrier depression 38 may be smaller than or similar to the size of the polishing beads in the slurry used for polishing. If the barrier depression 38 is too deep, the polisher cannot move the beads to polish the gel material 34 from the interstitial regions 16. In some examples, the barrier depression 38 has a depth that is greater than the depth of the nano-depressions 14 (as shown in FIG. 4(*ii*)). As an example, the barrier depression 38 has a depth that is at least 2 times greater than the depth of the nano-depressions 14. As other examples, the barrier depression 38 has a depth that is at least 10 times, or at least 100 times greater than the depth of the nano-depressions 14.

The barrier depression 38 is defined in a portion of the substrate surface $S_{12}$ and ultimately supports the hydrophobic barrier 20D that is ultimately formed. In other words, during the method, the hydrophobic barrier 20D is formed in the barrier depression 38. As such, the barrier depression 38 has the shape/configuration and X- and Y-dimensions that are desired for the hydrophobic barrier 20D, and defines a perimeter (see, e.g., FIG. 11) around each of the sub-sets 18A, 18B of the nano-depressions 14.

The non-patterned substrate 12' may be patterned to form the various features 14, 16, 38. Patterning may involve any of the examples set forth herein in reference to FIG. 1.

This example of the method includes applying a hydrophobic material on the patterned substrate 12, thereby introducing the hydrophobic material 22 i) into the barrier depression 38 and ii) into the nano-depressions 14. In this example, it is desirable to fill or underfill the depressions 14, 38 so that the hydrophobic material does not extend onto the interstitial regions 16. In this example, the hydrophobic material 22 may be co-planar with the interstitial regions 16. Any example of the hydrophobic materials disclosed herein may be used, and any suitable technique to selectively apply the hydrophobic material may be used. In a specific example, the hydrophobic material is one of the polymers in the CYTOP® series.

This example of the method also includes removing the hydrophobic material 22 at least from the nano-depressions 14, whereby at least some of the hydrophobic material 22 remains in the barrier depression 38. Removal of the hydrophobic material 22 from the nano-depressions 14 may involve etching. In examples, plasma etching with air or oxygen ($O_2$) gas may be used, or dry etching with oxygen ($O_2$) gas may be used. The substrate 12 may have a different etch rate than the hydrophobic material layer 22, so that the underlying substrate 12 (e.g., at the nano-depressions 14) acts as an etch stop once the second portion(s) 32 of the hydrophobic material layer 22 are removed herefrom.

This removal process exposes the nano-depressions 14 (as shown in FIG. 4(iv)) and may remove some of the hydrophobic material 22 from the barrier depression 38. However, due to the increased depth of the barrier depression 38 relative to the nano-depressions 14, it is to be understood that etching does not remove all of the hydrophobic material 22 from the barrier depression 38.

Exposure to etching may render the hydrophobic material 22 in the barrier depression 38 more hydrophilic. In one example to recover the hydrophobicity, the method involves exposing the surface of the hydrophobic material 22 in the barrier depression 38 to a high temperature process. This process may involve exposing the hydrophobic material 22 to a temperature ranging from about 80° C. to about 200° C., depending upon the hydrophobic material used. The recovery process may be a reflow process which involves a solvent, which may contain the same hydrophobic material deposited to introduce the material 22. The solvent reflow may be performed as a liquid phase process or as a vapor phase process. Liquid phase reflow may involve depositing the hydrophobic material solution on the hydrophobic material layer 22 in the barrier depression 38 at a high temperature (for example, 180° C.), and then curing at a lower temperature (for example, 50° C.). Vapor phase reflow may involve placing the substrate 12 (with the hydrophobic material 22 in the barrier depression 38) into a vacuum-sealed desiccator with some amount of the hydrophobic material solution in it. The hydrophobicity is restored as a result of the recovery or reflow process, and the hydrophobic barrier 20D is formed. High temperature recovery or reflow may also be performed after the gel material 34 is deposited and polished, as reflow does not deleteriously impact the gel material 34 for sequencing.

This example method also involves attaching a gel material 34 to the nano-depressions 14 of the respective sub-sets 18A, 18B, as shown in FIG. 4(v). As an example, attaching the gel material 34 involves silanizing the nano-depressions 14 and interstitial regions 16 of the respective sub-sets 18A, 18B, and depositing the gel material 34 on the nano-depressions 14 and interstitial regions 16 of the respective sub-sets 18A, 18B. This example of the method further includes removing the gel material 34 from the interstitial regions 16, as shown in FIG. 4(vi). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14 and without deleteriously affecting the hydrophobic barrier 20D. Polishing may be performed as described herein in reference to FIG. 1.

The hydrophobic barrier 20D is capable of remaining intact after polishing. In this example, hydrophobic barrier 20D is formed in the barrier depression 38. As depicted in FIG. 4(vi), a surface $S_{20D}$ of the hydrophobic barrier 20D does not extend outward in the Z-direction above the interstitial regions 16, and thus the hydrophobic barrier 20D is co-planar with the interstitial regions 16. In this example, the thickness of the hydrophobic barrier 20D corresponds with the depth of the barrier depression 38, and no portion of the thickness extends beyond the interstitial regions 16.

The portion of the flow cell 10D shown in FIG. 4(vi) also has primers 36 grafted to the gel material 34 in the depressions 14 of the sub-sets 18A, 18B. Any of the primers 36 and the grafting processes described in reference to FIG. 1 may be used.

Figure 5:
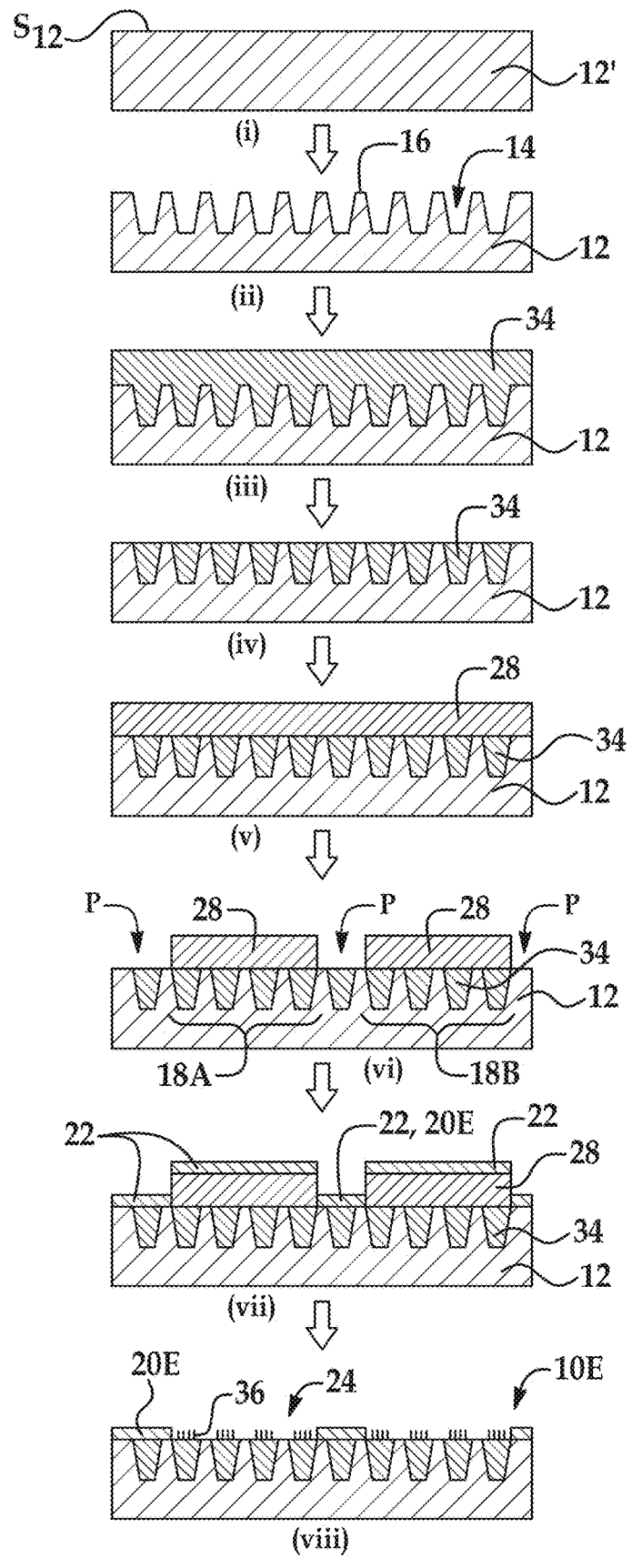
FIG. 5 is a schematic flow diagram including (i) through (viii) illustrating yet a further example of the methods disclosed herein to form yet a further example of the flow cell disclosed herein.

Referring now to FIG. 5, an example of the method for forming the hydrophobic barrier 20E is schematically depicted. In this example method, a patterned substrate 12 is used (FIG. 5(ii)), or is generated from a non-patterned substrate 12' as part of the method (FIG. 5(i) through FIG. 5(ii)).

This example method also involves attaching a gel material 34 to the nano-depressions 14 and on the interstitial regions 16, as shown in FIG. 5(iii). As an example, attaching the gel material 34 involves silanizing the nano-depressions 14 and interstitial regions 16, and depositing the gel material 34 on the nano-depressions 14 and interstitial regions 16. This example of the method further includes removing the gel material 34 from the interstitial regions 16, as shown in FIG. 5(iv). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14. Polishing may be performed as described herein in reference to FIG. 1.

The mask material 28 is then applied on the patterned substrate 12 having the gel material 34 in the nano-depressions 14, as shown in FIG. 5(v). The mask material 28 may be applied to define a pattern P for a hydrophobic barrier around respective sub-sets 18A, 18B of the nano-depressions 14 and interstitial regions 16, as shown in FIG. 5(vi).

In an example, the selective application of the mask material 28 may involve depositing the material 28 on the gel material 34 in the nano-depressions 14 and on the interstitial regions 16, and patterning the material 28, e.g., by photolithography, so that the pattern P is defined. In one example, patterning of the mask material 28 may be performed as described in reference to FIG. 1. In another example, the mask material 28 is a bi-layer resist including a lift-off layer and an imaging layer. Photolithography may be used to pattern the imaging layer, and then any portions of the lift-off layer that are exposed at the pattern P can be removed by an ashing process. This will expose some portions of the patterned substrate 12.

This example of the method includes applying a hydrophobic material according to the pattern P, as shown in FIG. 5(vii). The hydrophobic material 22 deposited according to the pattern P forms the hydrophobic barrier 20E on exposed portions of the patterned substrate 12. The hydrophobic material 22 is deposited to have a thickness less than about 2 µm, and thus the hydrophobic barrier 20E has a thickness less than about 2 µm. Any example of the hydrophobic materials disclosed herein may be used, and any suitable technique to applying the hydrophobic material may be used.

As shown in FIG. 5(vii), the hydrophobic material 22 may also be deposited on the remaining mask material 28. The mask material 28 may be removed via any of the techniques described herein in reference to FIG. 1, and the hydrophobic material 22 on the mask material 28 may also be removed during this process (see FIG. 5(viii)). The removal of the mask material 28 (and any hydrophobic material 22 thereon) reveals the sub-sets of nano-depressions 14 having the gel material 34 therein.

The portion of the flow cell 10E shown in FIG. 5 also has primers 36 grafted to the gel material 34 in the depressions 14 of the sub-sets 18A, 18B. Any of the primers 36 and the grafting processes described in reference to FIG. 1 may be used.

Figure 6:
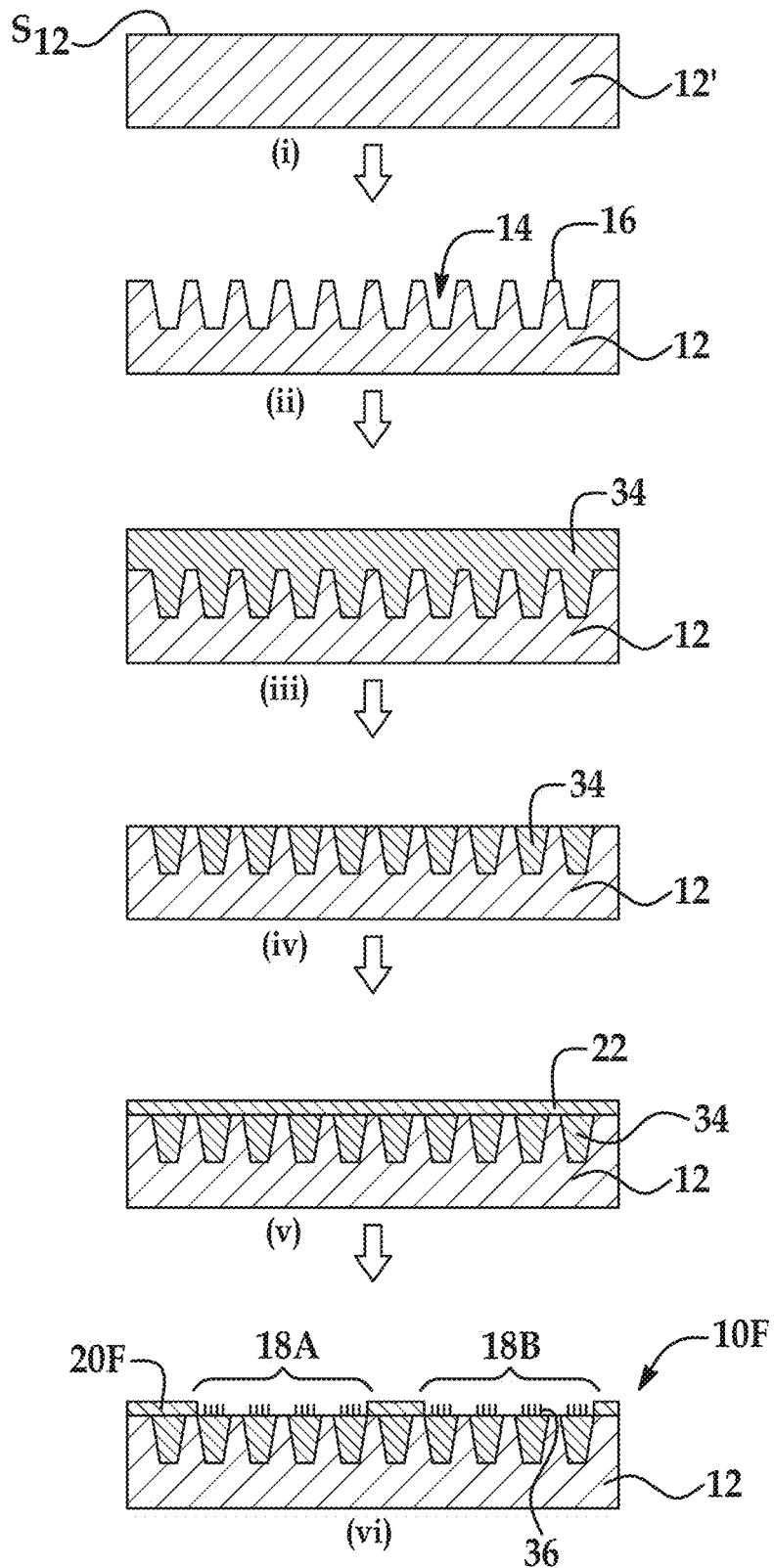
FIG. 6 is a schematic flow diagram including (i) through (vi) illustrating still another example of the methods disclosed herein to form still another example of the flow cell disclosed herein.

Referring now to FIG. 6, an example of the method for forming the hydrophobic barrier 20F is schematically depicted. In this example method, a patterned substrate 12 is used (FIG. 6(*ii*)), or is generated from a non-patterned substrate 12' as part of the method (FIG. 6(*i*) through FIG. 6(*ii*)).

This example method also involves attaching a gel material 34 to the nano-depressions 14 and on the interstitial regions 16, as shown in FIG. 6(*iii*). As an example, attaching the gel material 34 involves silanizing the nano-depressions 14 and interstitial regions 16, and depositing the gel material 34 on the nano-depressions 14 and interstitial regions 16. This example of the method further includes removing the gel material 34 from the interstitial regions 16, as shown in FIG. 6(*iv*). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14. Polishing may be performed as described herein in reference to FIG. 1.

In this example, as shown in FIG. 6(*v*), the hydrophobic material layer 22 is a film that can be laminated to the patterned substrate 12 having the gel material in the nano-depressions 14. The hydrophobic material layer/film 22 has a thickness less than about 2 µm. Any example of the hydrophobic materials disclosed herein may be used.

Photolithography may then be used to pattern the hydrophobic material layer/film 22 to form the hydrophobic barrier 20F around respective sub-sets 18A, 18B of the nano-depressions 14 and the interstitial regions 16. This is shown in FIG. 6(*vi*).

The portion of the flow cell 10F shown in FIG. 6(*vi*) also has primers 36 grafted to the gel material 34 in the depressions 14 of the sub-sets 18A, 18B. Any of the primers 36 and the grafting processes described in reference to FIG. 1 may be used.

Figure 7:
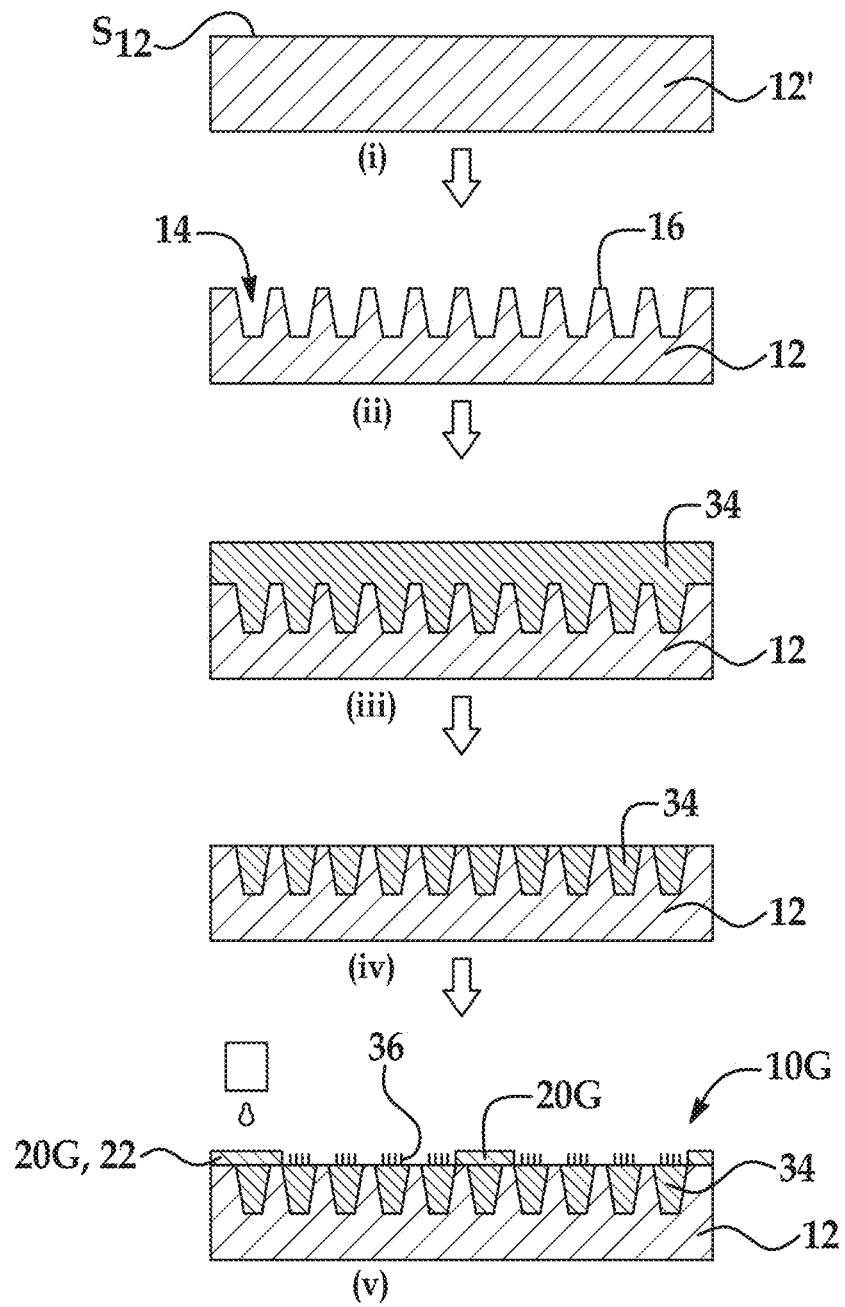
FIG. 7 is a schematic flow diagram including (i) through (v) illustrating another example of the methods disclosed herein to form another example of the flow cell disclosed herein.

Referring now to FIG. 7, an example of the method for forming the hydrophobic barrier 20G is schematically depicted. In this example method, a patterned substrate 12 is used (FIG. 7(*ii*)), or is generated from a non-patterned substrate 12' as part of the method (FIG. 7(*i*) through FIG. 7(*ii*)).

This example method also involves attaching a gel material 34 to the nano-depressions 14 and on the interstitial regions 16, as shown in FIG. 7(*iii*). As an example, attaching the gel material 34 involves silanizing the nano-depressions 14 and interstitial regions 16, and depositing the gel material 34 on the nano-depressions 14 and interstitial regions 16. This example of the method further includes removing the gel material 34 from the interstitial regions 16, as shown in FIG. 7(*iv*). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14. Polishing may be performed as described herein in reference to FIG. 1.

In this example, the hydrophobic material is deposited by printing, as shown in FIG. 7(*v*). The hydrophobic material may be dispersed in a suitable carrier liquid, and then printed using aerosol printing or inkjet printing. The hydrophobic material is printed in a pattern that is desirable for the hydrophobic barrier 20G. The hydrophobic barrier 20G has a thickness less than about 2 µm. Any example of the hydrophobic materials disclosed herein may be used.

The portion of the flow cell 10G shown in FIG. 7(*v*) also has primers 36 grafted to the gel material 34 in the depressions 14 of the sub-sets 18A, 18B. Any of the primers 36 and the grafting processes described in reference to FIG. 1 may be used.

Figure 8:
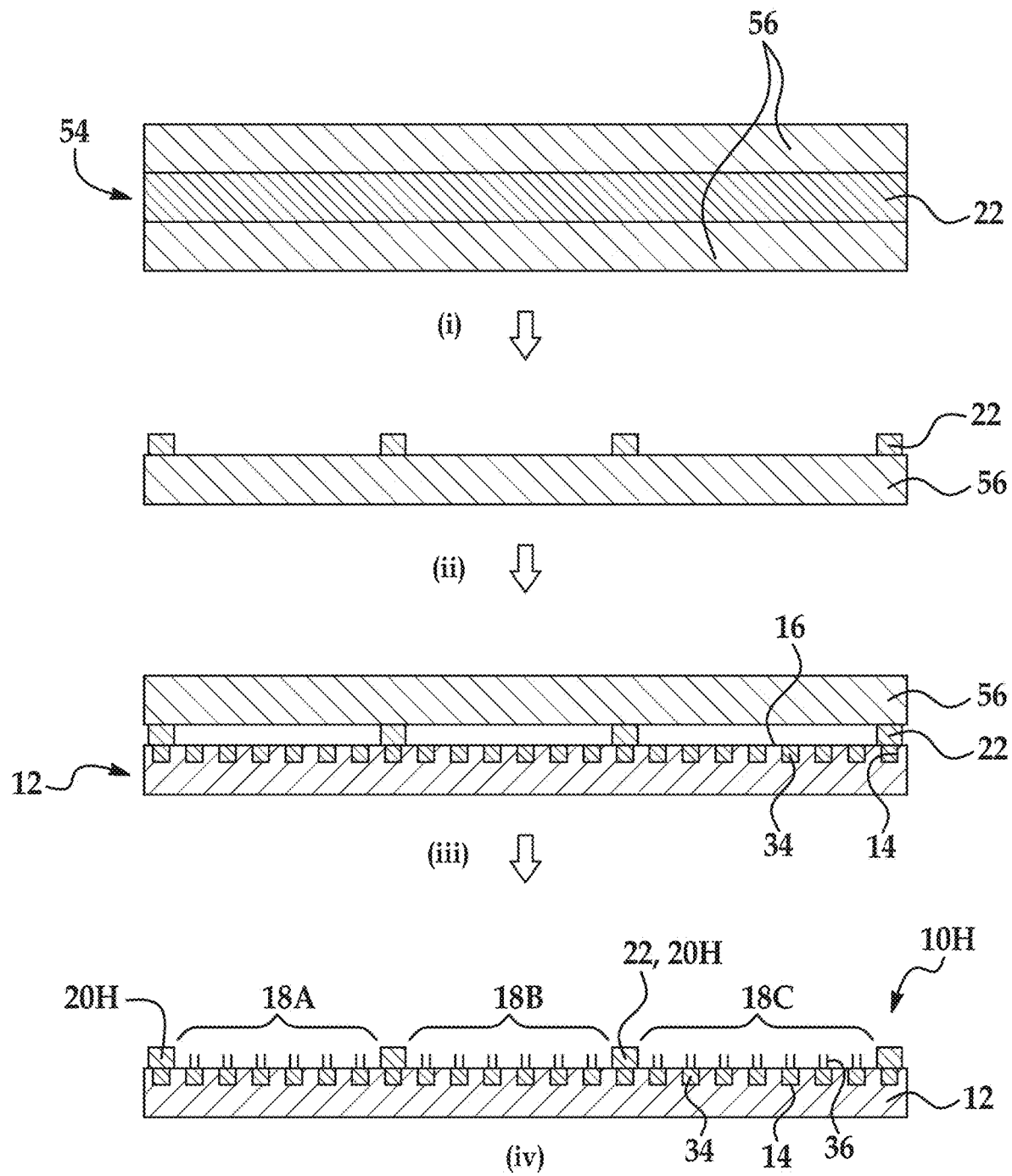
FIG. 8 is a schematic flow diagram including (i) through (iv) illustrating a further example of the methods disclosed herein to form a further example of the flow cell disclosed herein.

Referring now to FIG. 8, an example of the method for forming the hydrophobic barrier 20H is schematically depicted. In this example method, a patterned substrate 12 is used (FIG. 8(*iii*)), or is generated from a non-patterned substrate 12' as part of the method.

This example method also involves attaching a gel material 34 to the nano-depressions 14 and on the interstitial regions 16 (FIG. 8(*iii*)). As an example, attaching the gel material 34 involves silanizing the nano-depressions 14 and interstitial regions 16, and depositing the gel material 34 on the nano-depressions 14 and interstitial regions 16. This example of the method further includes removing the gel material 34 from the interstitial regions 16 (FIG. 8(*iii*)). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14. Polishing may be performed as described herein in reference to FIG. 1.

This example method utilizes a transfer lamination process to form the hydrophobic barrier 20H.

As shown at FIG. 8(*i*), a multi-layer precursor 54 includes two sacrificial layers 56 and the hydrophobic material layer 22 (having a thickness less than about 2 µm) positioned between the two sacrificial layers 56. Any example of the hydrophobic materials disclosed herein may be used, and examples of the sacrificial layers include adhesive materials that can be peeled off of the hydrophobic material. In an example, the sacrificial layers 56 include polyethylene terephthalate (PET). This multi-layer precursor 54 may be processed using laser cutting and weeding. Laser cutting may involve a direct-write method or a mask-projection method. The laser cutting and weeding process removes a first of the sacrificial layers 56 and defines a pattern of a hydrophobic barrier 20H in the hydrophobic material layer 22 that is positioned on the second of the sacrificial layers 56, as shown in FIG. 8(*ii*).

The patterned hydrophobic material layer 22 is put into contact with the patterned substrate 12 having the gel material 34 in the nano-depressions 14, as shown in FIG. 8(*iii*). The patterned hydrophobic material layer 22 transfers to the patterned substrate 12, and the second of the sacrificial layers 56 can then be removed by peeling it away. The transfer forms the hydrophobic barrier 20H around respective sub-sets 18A, 18B, 18C of the nano-depressions 14 and the interstitial regions 16, as shown in FIG. 8(*iv*).

The portion of the flow cell 10H shown in FIG. 8(*iv*) also has primers 36 grafted to the gel material 34 in the depressions 14 of the sub-sets 18A, 18B, 18C. Any of the primers 36 and the grafting processes described in reference to FIG. 1 may be used.

Figure 9:
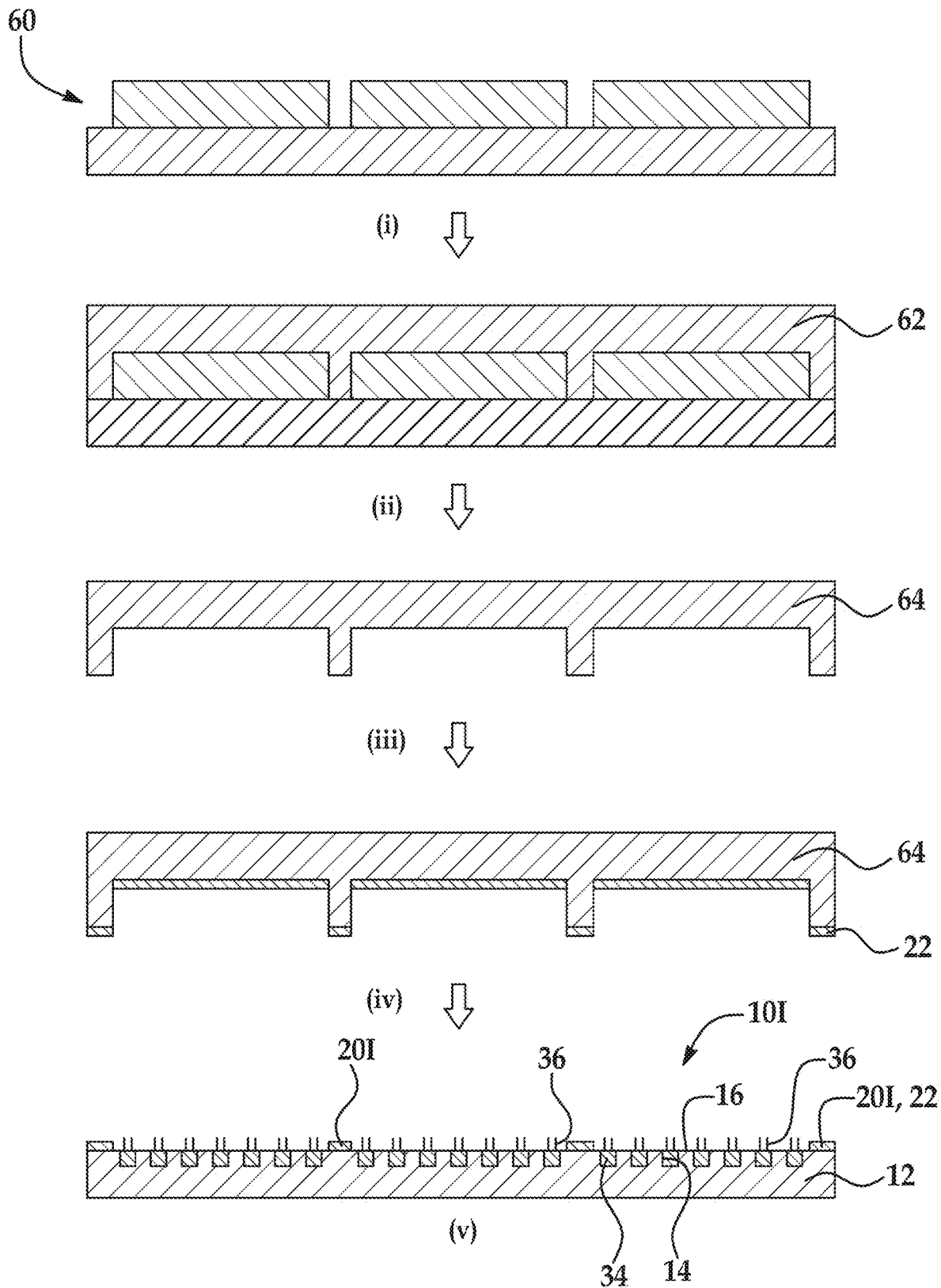
FIG. 9 is a schematic flow diagram including (i) through (v) illustrating still another example of the methods disclosed herein to form still another example of the flow cell disclosed herein.

Referring now to FIG. 9, an example of the method for forming the hydrophobic barrier 20I is schematically depicted. In this example method, a patterned substrate 12 is used (FIG. 9(v)), or is generated from a non-patterned substrate 12' as part of the method.

This example method also involves attaching a gel material 34 to the nano-depressions 14 and on the interstitial regions 16 (FIG. 9(v)). As an example, attaching the gel material 34 involves silanizing the nano-depressions 14 and interstitial regions 16, and depositing the gel material 34 on the nano-depressions 14 and interstitial regions 16. This example of the method further includes removing the gel material 34 from the interstitial regions 16 (FIG. 9(v)). In this example, the gel material 34 may be exposed to polishing. Polishing can remove the gel material 34, and in some instances, at least part of the silane or silane derivative, from the interstitial regions 16 without deleteriously affecting the gel material 34 in the nano-depressions 14. Polishing may be performed as described herein in reference to FIG. 1.

This example method utilizes a transfer process to form the hydrophobic barrier 20I.

As shown at FIG. 9(i), a master template 60 is used which has the same pattern that is desirable for the hydrophobic barrier 20I. The master template 60 may be silicon.

A working stamp material 62 may then be deposited on the master template 60 and cured to form a working stamp 64, as shown in FIG. 9(ii) through FIG. 9(iii). The working stamp material may include silicon acrylate monomers, polydimethylsiloxane (PDMS), etc. The working stamp 64 may be removed, and a thin layer of the hydrophobic material 22 may be applied thereto, as shown in FIG. 9(iv). Any example of the hydrophobic materials disclosed herein may be used, and the thin layer has a thickness of 2 μm or less.

Portions of the hydrophobic material 22 on the working stamp 64 are put into contact with the patterned substrate 12 having the gel material 34 in the nano-depressions 14. The working stamp 64 transfers the portions of the hydrophobic material layer 22 to the patterned substrate 12. The transfer forms the hydrophobic barrier 20I around respective sub-sets 18A, 18B, 18C of the nano-depressions 14 and the interstitial regions 16, as shown in FIG. 9(v).

The portion of the flow cell 10I shown in FIG. 9(v) also has primers 36 grafted to the gel material 34 in the depressions 14 of the sub-sets 18A, 18B, 18C. Any of the primers 36 and the grafting processes described in reference to FIG. 1 may be used.

Figure 10:
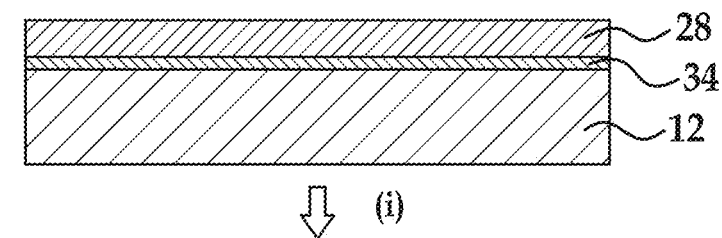
FIG. 10 is a schematic flow diagram including (i) through (iv) illustrating still another example of the methods disclosed herein to form still another example of the flow cell disclosed herein.
Figure 10:
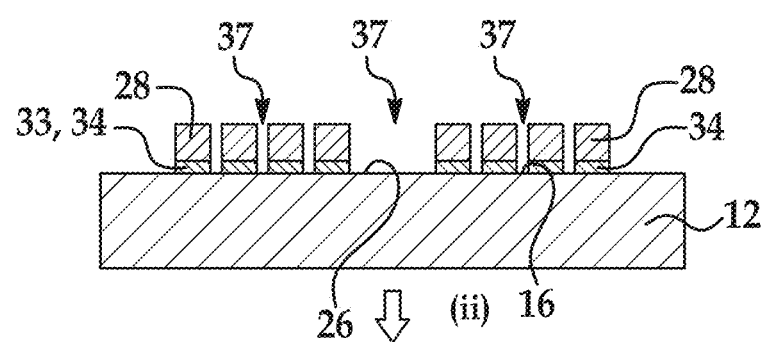
Figure 10:
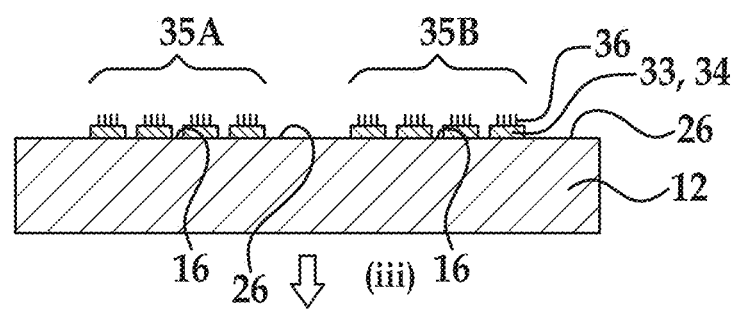
Figure 10:
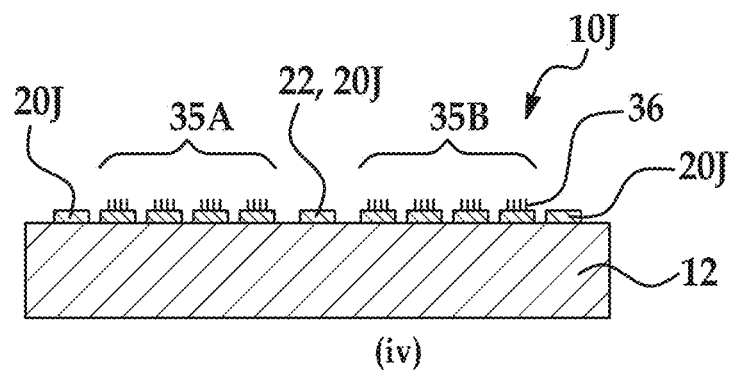

Another example of a flow cell 10J is shown in FIG. 10(iv). In this example, the flow cell 10J includes: a substrate 12, nano-pads 33 of a gel material 34 positioned on the substrate 12; and a hydrophobic material layer 22 i) having a surface that is at least substantially co-planar with a surface of the nano-pads 33 and ii) positioned to define a hydrophobic barrier 20J around respective sub-sets 35A, 35B of the nano-pads 33. In an example, each of the nano-pads 33 has a thickness less than about 2 μm, and the hydrophobic material layer 22 (hydrophobic barrier 20J) has a thickness less than about 2 μm.

Any examples of the substrate 12 described herein may be used in this example flow cell 10J.

The nano-pads 33 are islands (e.g., circular, triangular, rectangular, etc. in shape, e.g., from a top view) of gel material 34 that are spatially separated from one another. Any example of the gel material 34 disclosed herein may be used in the nano-pads 33. Primer(s) 36 may also be attached to each of the nano-pads 33. Any examples of the primers 36 disclosed herein may be used.

The nano-pads 33 may be distributed across the substrate 12 in any suitable pattern or layout. Sub-sets 35A, 35B of the nano-pads 33 may be separated by the hydrophobic barrier 20J. The pattern of nano-pads 33 in each sub-set 35A, 35B may be the same; or different patterns of nano-pads 33 may be used in different sub-sets 35A, 35B. Many different patterns/layouts of the nano-pads 33 may be envisaged, including regular, repeating, and non-regular patterns. In an example, the nano-pads 33 are disposed in a hexagonal grid for close packing and improved density. Other layouts may include, for example, parallelogram layouts (i.e., rectangular, square, etc.), triangular layouts, circular layouts, and so forth.

Each nano-pad 33 may have any suitable shape (and corresponding 3-dimensional geometry), such as a circle, an oval, a polygon (e.g., triangle, quadrilateral, pentagon, etc.), etc.

The size of each nano-pad 33 may be characterized by its diameter, and/or length and width. In some instances, the diameter or length and width of each nano-pad 33 can be at least about 1 nm, 50 nm, about 100 nm, about 500 nm, up to about 2 μm. An example of the nano-pad 33 diameter ranges from about 1 nm to about 500 nm. Another example of the nano-pad 33 diameter ranges from about 300 nm to about 1 μm.

The nano-pad 33 may also have a thickness. As examples, the thickness of each nano-pad 33 can be less than 2 μm.

Adjacent nano-pads 33 are separated by the interstitial regions 16 within a given sub-set 35A, 35B. The sub-sets 35A, 35B are separated by an example of the hydrophobic barrier 20J. The average nano-pad pitch represents the spacing from the center of one nano-pad 33 to the center of an adjacent nano-pad 33 (center-to-center spacing) or from the edge of one nano-pad 33 to the edge of an adjacent nano-pad 33 (edge-to-edge spacing). Any of the pitches described herein for the nano-depressions may be applicable for the nano-pads.

This example of the flow cell 10J also includes the hydrophobic barrier 20J. Any example of the hydrophobic materials disclosed herein may be used. Any suitable technique may be used that is capable of applying the hydrophobic material as a thin film.

Together, FIG. 10(i) through FIG. 10(iv) illustrate an example of a method for making the flow cell 10J. In this example, the method comprises forming discrete subsets 35A, 35B of nano-pads 33 on the substrate 12, each of the nano-pads 33 having a thickness less than about 2 μm (see FIG. 10(i) through FIG. 10(iii)); and selectively applying a hydrophobic material 22 on the substrate 12 around each of the discrete subsets 35A, 35B, thereby forming a hydrophobic barrier 20J i) around each of the discrete subsets 35A, 35B, ii) having a surface that is at least substantially co-planar with a surface of the nano-pads 33, and iii) having a thickness less than about 2 μm.

Any suitable technique may be used to form the discrete subsets of nano-pads 33. In one example, the method involves applying a gel material 34 on a surface of the substrate 12 (FIG. 10(i)); disposing a mask material 28 on the gel material 34 (FIG. 10(i)); forming spaces 37 in the mask material 28 and the gel material 34; and removing the mask material 28 (FIG. 10(iii)).

Applying the gel material 34 may be performed as described using any of the techniques disclosed herein. For example, the surface of the substrate 12 may be silanized and the gel material 34 may be deposited using any of the techniques disclosed herein. The mask material 28 is then applied on the gel material 34 using any of the techniques disclosed herein.

The spaces 37 (which become interstitial regions 16 between the nano-pads or a barrier interstitial 26 on which the hydrophobic barrier 20J is formed) are then formed in the mask material 28 and the underlying gel material 34. The spaces 37 may be formed by patterning the material 28, e.g., by photolithography, and removing the patterned portion using a developer solution. At this point, portions of the mask material 28 are removed and the underlying portions of the gel material 34 at the spaces 37 are exposed. Etching may be used to remove these portions of the gel material 34 and to fully define the spaces 37 (as shown in FIG. 10(*ii*)). The remaining portions of the mask material 28 may be lifted off in accordance with any of the examples set forth herein (e.g., using a suitable reagent).

As shown in FIG. 10(*iii*), removal of the mask material 28 exposes the nano-pads 33. Primers 36 may then be attached using any of the example grafting techniques disclosed herein.

This example of the method includes applying a hydrophobic material 22 on the substrate 12 around each of the discrete subsets 35A, 35B of nano-pads 33, thereby forming a hydrophobic barrier 20J as shown in FIG. 10(*iv*). In an example, the selective application of the hydrophobic material 22 involves transferring the hydrophobic material 22 in a pattern of the hydrophobic barrier 20J to the substrate 12. This example utilizes a transfer lamination process as described in reference to FIG. 8 or a transfer process as defined in FIG. 9. In another example, the selective application of the hydrophobic material 22 involves printing the hydrophobic material in a pattern of the hydrophobic barrier to the substrate. This example utilizes a printing process as described in reference to FIG. 7(*v*). In another example, the selective application of the hydrophobic material 22 involves applying a (second) mask material (not shown) on the discrete subsets 35A, 35B of nano-pads 33, thereby defining a pattern for the hydrophobic barrier 20J; applying the hydrophobic material 22 according to the pattern, thereby forming the hydrophobic barrier 20J; and removing the mask material. This example utilizes the processes described in reference to FIG. 5(*vi*) through FIG. 5(*viii*). In this particular example, it may be desirable to graft the primers 36 after the hydrophobic barrier 20J.

Figure 11:
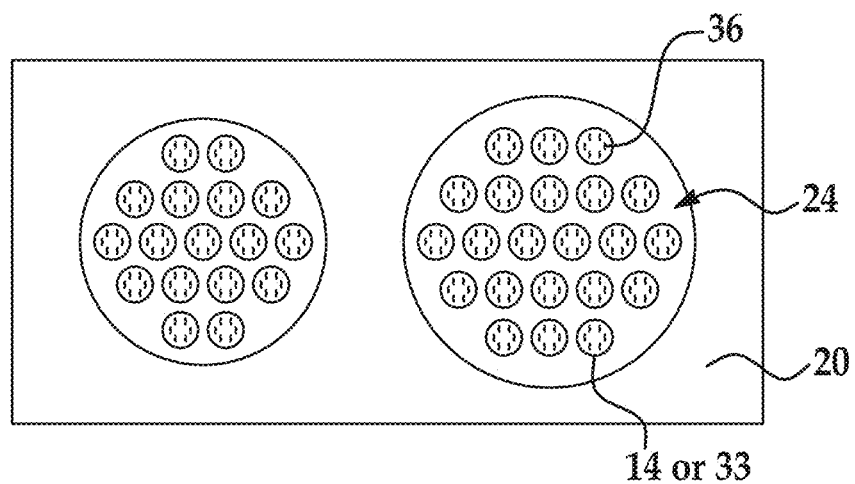
FIG. 11 is a top view of a portion of an example flow cell formed by the any of the methods described in FIG. 1 through FIG. 10.

FIG. 11 depicts a top view of a portion of any of the example flow cells 10A-10J formed via the methods described herein. As illustrated, each of the hydrophobic barriers 20A-20I (shown generally as "20" in FIG. 11) defines a perimeter of a chamber 24 in which the nano-depressions 14 are defined, and the hydrophobic barrier 20J (again, shown generally as "20") defines a perimeter of a chamber 24 in which the nano-pads 33 are defined.

While not shown in the FIG. 1 through FIG. 11, it is to be understood that each of the flow cells 10A-10J may also include a capture site in each chamber 24. The capture site is physically and/or chemically capable of immobilizing a complex within a particular chamber 24. The capture site may be positioned at any suitable location within the chamber 24, which may depend upon the arrangement of the nano-depressions 14 or nano-pads 33. The position of the capture sites across the substrate 12 or 12' may be uniform (e.g., each capture site is in substantially the same position (e.g., center, far left, etc.) within each chamber 24) or may be non-uniform (e.g., the captures sites are in different positions within the different chambers 24). The capture site may have any suitable shape, geometry and dimensions, which may depend, at least in part, on the configuration of the capture site (e.g., a patch, a well, a protrusion, etc.), the dimensions of the chamber 24 in which the capture site is formed, and the type of complex that is to be captured by the capture site.

In some examples, the capture site is a chemical capture agent that is applied on a portion of the interstitial regions 14. Any examples of the chemical capture agent disclosed herein may be used. In one example, the chemical capture agent may be deposited in a desirable location using microcontact printing, or another suitable technique.

In other examples, the capture site includes a well that is defined in the surface $S_{12}$ of the substrate 12. The wells may be formed in the surface $S_{12}$ using etching or imprinting depending upon the substrate 12 that is used. In an example, the wells may be formed at the same time as the nano-depressions 14, or may be formed prior to the nano-pads 33. The wells may have any suitable shape and geometry, and may be larger than the nano-depressions 14 or the nano-pads 33 but smaller than the chamber 24.

In some examples, the wells do not have an additional chemical capture agent added thereto. In these examples, the opening dimensions enable the complexes to self-assemble into the wells and, in some examples, not the depressions 14 by size exclusion. In other examples, the wells do have an additional chemical capture agent added thereto.

Other examples of the capture site include the well and a capture bead having a chemical capture agent on a surface thereof. The capture bead may be sized to fit into the wells and, in some examples, not the depressions 14. In some examples, the capture bead may be co-planar with or extend slightly above the adjacent interstitial regions 16 so that the complex that ultimately attaches thereto is not confined within the well. In an example, the capture bead is selected from the group consisting of silicon dioxide, a superparamagnetic material, polystyrene, and an acrylate. Any examples of the chemical capture agent disclosed herein may be used on the surface of the capture bead, and may be coated on the capture bead before it is introduced into the well.

The depth of the capture site well may vary depending upon whether the chemical capture agent is to be introduced thereto and whether the capture bead is to be introduced thereto. The depth may be selected at least to accommodate these materials (i.e., the material is contained within the well 30). In an example, the depth of the well ranges from about 1 nm to about 5 μm.

Also while not shown in FIG. 1 through FIG. 10, it is to be understood that a lid or a second substrate 12 may be bonded to the substrate 12 directly, or may be bonded to the substrate 12 through the hydrophobic barrier 20A-20J. The lid may be positioned so that it defines a single flow channel (in fluid communication with the plurality of chambers 24) or multiple, fluidically separated flow channels (each of which is in fluid communication with a sub-set of the plurality of chambers 24).

The lid may be any material that is transparent to an excitation light that is directed toward the nano-depression(s) 14. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid or second substrate 12 may be bonded using any suitable technique, such as laser bonding, diffusion bonding, anodic bonding, eutectic bonding, plasma activation bonding, glass frit bonding, UV curable or other adhesives, or others methods known in the art. In an example, a spacer layer may be used to bond the lid to the portion of the hydrophobic barrier 20A, 20B, 20C, 20DI. The spacer layer may be any material that will seal at least some of the hydrophobic barrier 20A, 20B, 20C, 20D and the lid together.

While not shown, it is to be understood that one or more additional layers may be incorporated between the substrate 12 and the lid or the second substrate 12, or between the substrate 12 and the nano-depressions 14. These additional layer(s) may be selected to function as a planar waveguide for the excitation of the nano-depressions 14 with an evanescent field.

Complexes for Use with Flow Cells

Figure 12A:
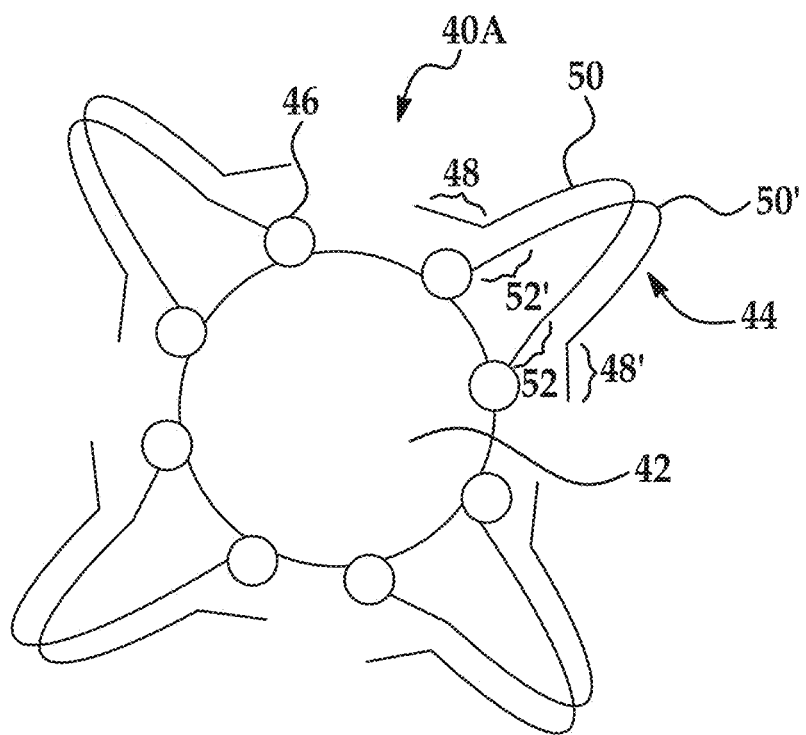
FIGS. 12A through 12C are schematic illustrations of different examples of DNA-bead or hydrogel complexes that can be used with the examples of the flow cells disclosed herein.
Figure 12B:
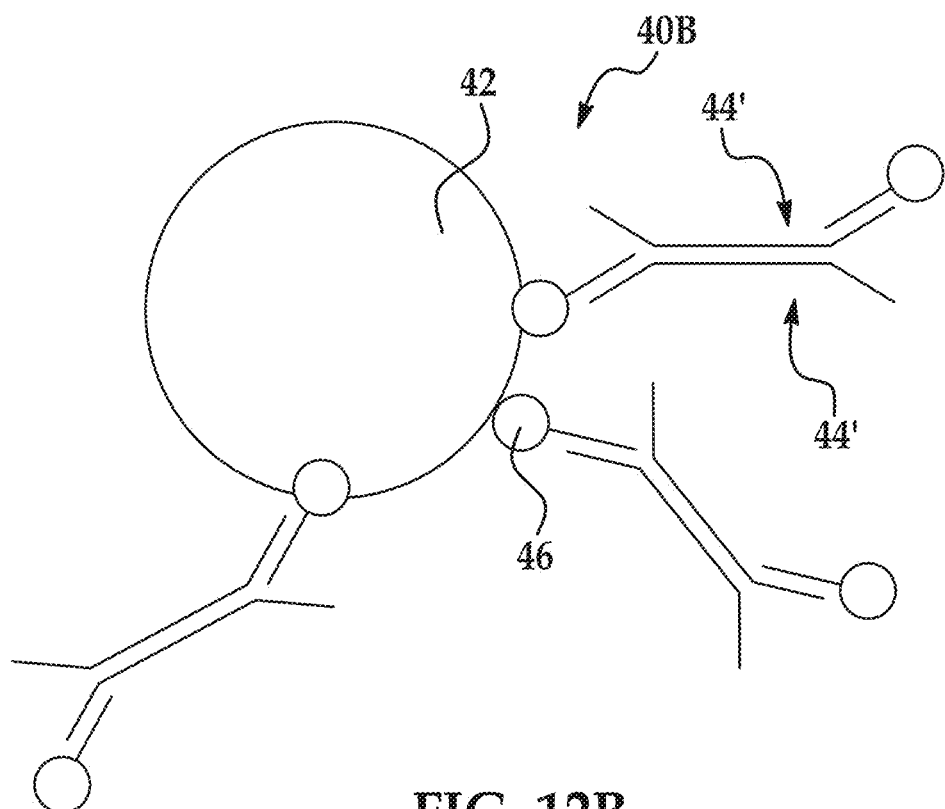
Figure 12C:
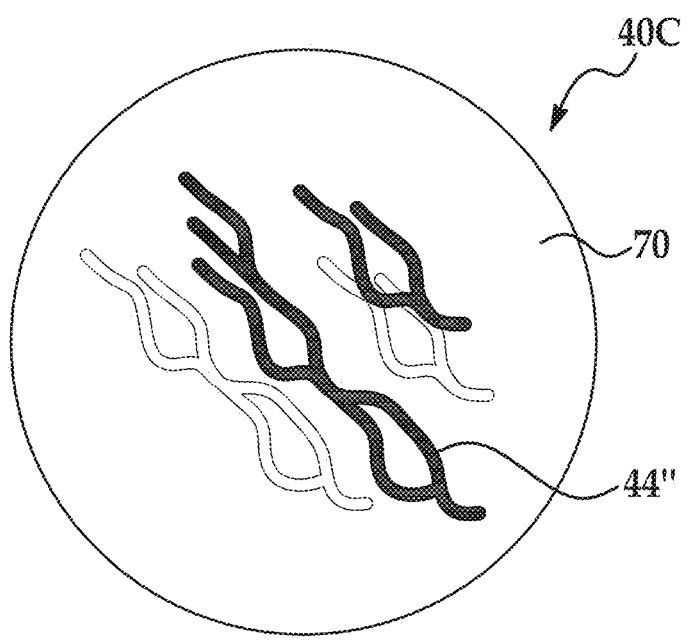
Figure 13C:
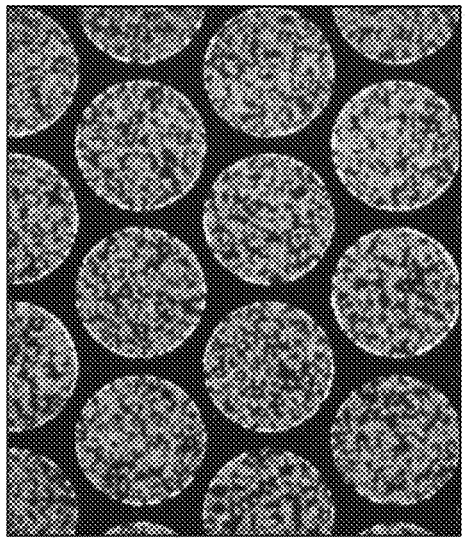
FIGS. 13A through 13F are black and white fluorescence microscopy images of different examples of the micro-chamber geometries defined by respective hydrophobic material layers having a thickness of about 2 µm, after staining the DNA clusters inside the micro-chamber geometries with DNA intercalator dye (e.g., SYTOX)
Figure 13B:
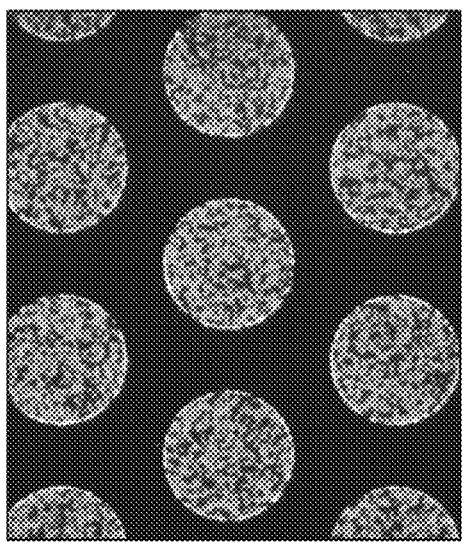
Figure 13A:
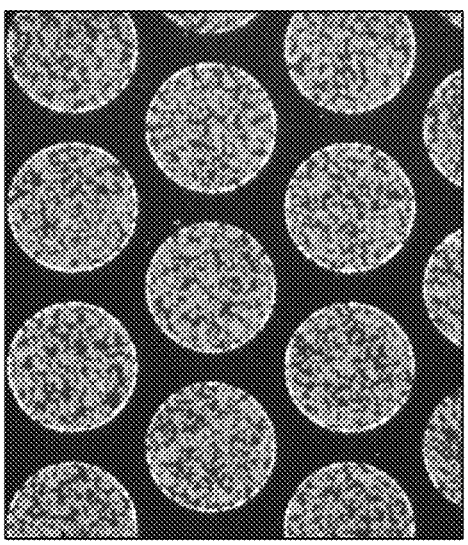
Figure 13F:
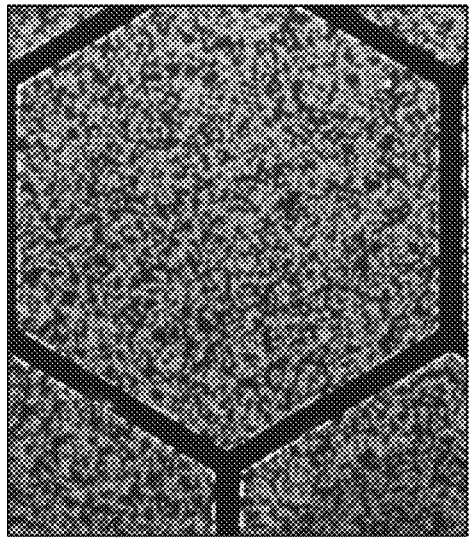
Figure 13E:
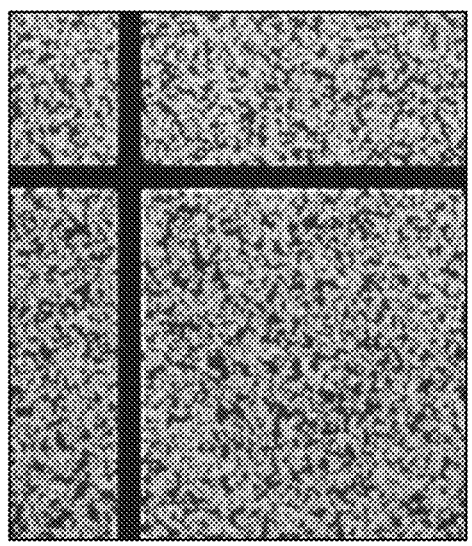
Figure 13D:
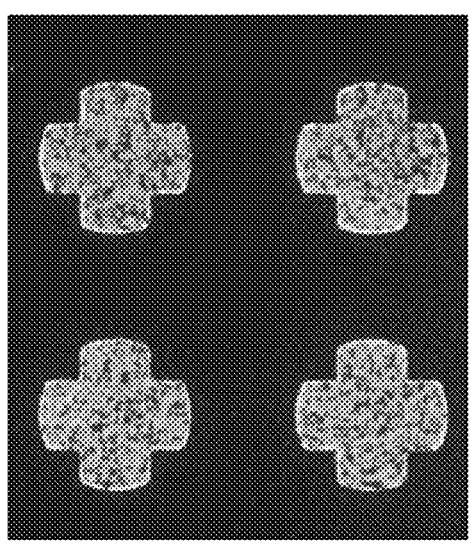

The flow cells 10A-10J may be suitable for use with examples of the complexes disclosed herein. As noted herein, a complex includes a carrier (e.g., a hydrogel support or a solid support) and sequencing-ready nucleic acid fragments attached to or contained within the carrier. Examples of suitable complexes are shown in FIG. 12A through FIG. 12C. While some example methods for making the complexes are described, it is to be understood that other methods may be used as long as sequencing-ready nucleic acid fragments attached to or contained within the carrier FIG. 12A illustrates a complex 40A that includes a solid support 42 and sequencing-ready nucleic acid fragments 44 attached to the solid support 42.

In one example, to form this complex 40A, an adapter sequence (52, 52') is bound to the solid support 42 through one member 46 of a binding pair. In an example, this adapter sequence includes a first sequencing primer sequence (e.g., a read 1 sequencing primer sequence), a first sequence (e.g., a P5' sequence) that is complementary to at least a portion of one of the primers 36 on the flow cell 10A-10I. As mentioned, this adapter sequence is bound to the one member 46 of the binding pair (e.g., biotin) so that it can be bound to the surface of the solid support 42 (which includes the other member (e.g., avidin, streptavidin, etc.) of the binding pair). This adapter sequence may also include an index sequence.

A Y-adapter may be mixed with a transposase enzyme (e.g., two Tn5 molecules) to form a transposome. The Y-adapter may include two mosaic end sequences that are hybridized to each other. One of the mosaic end sequences may be attached to a second sequencing primer sequence (e.g., a read 2 sequencing primer sequence), a second sequence (e.g., a P5' sequence) that is complementary to at least a portion of one of the primers 36 on the flow cell 10A-10I, and optionally an index/barcode sequence. Together, the second sequencing primer sequence and the second sequence make up adapter sequences 48, 48'.

A tagmentation process may then be performed. A fluid (e.g., a tagmentation buffer) including a sample (e.g., DNA) may be added to the transposomes and to the solid support 42 having the adapter sequence bound thereto. As the sample contacts the transposomes, the DNA is tagmented (fragmented and tagged with the adapter sequence 52, 52' on the solid support 42) and is bound to the Y-adapter (e.g., through ligation of the free mosaic end sequence). Successive tagmentation of the sample results in a plurality of bridged molecules between transposomes. To complete the sequencing ready fragments, further extension and ligation is undertaken to ensure fragments 50, 50' are attached to sequences 48 and 48'. The transposase enzyme may then be removed via sodium dodecyl sulfate (SDS) treatment or heat or proteinase K digestion.

The resulting complex 40A is shown in FIG. 12A. The bridged molecules are the sequencing-ready nucleic acid fragments 44, each of which includes a fragment 50, 50' and adapter sequences 48 and 52 or 48' and 50' attached at either end. The adapter sequences 52, 52' are those initially bound to the solids support 42, and include the first sequencing primer sequence, the first sequence complementary to the flow cell primer, and the one member 46 of a binding complex. The adapter sequences 48, 48' are from the Y-adapter, and include the second sequence complementary to another flow cell primer and the second sequencing primer sequence. Because each sequencing-ready nucleic acid fragment 44 includes suitable adapters for amplification (e.g., bridge amplification) and sequencing, PCR amplification is not performed. These fragments 44 are thus sequencing-ready. Moreover, because the library fragments 44 are from the same sample, the fragments 44 may be suitable for linked long read applications.

FIG. 12B illustrates another complex 40B that includes a solid support 42 and sequencing-ready nucleic acid fragments 44' attached to the solid support 42. In one example, a PCR-free nucleotide library is created in a tube, and then the library is hybridized to the solid support 42 in the tube. In the example shown in FIG. 12B, primers having one member of a binding pair are added to the library fragments in the tube, and then the sequencing-ready nucleic acid fragments 44' are bound to the solid support 42. In another example, the solid support 42 may have primers attached thereto via a binding pair (e.g., avidin on the support 42 and biotin attached to the primer). These primers hybridize to library fragments (and thus the primer and binding pair member are at one end of the fragments and not at the other). In another example, extension may be performed using a strand displacing enzyme. This will result in an entirely double stranded library (e.g., no fork or Y-adapter, as shown in FIG. 12B). The sequencing-ready nucleic acid fragments 44' may be released on the flow cell 10A,-10I via denaturation. Because the library fragments 44' are created prior to being attached to the solid support 42, the fragments 44' may not be from the same sample, and thus may not be suitable for linked long read applications.

FIG. 12C illustrates an example of the complex 40C that includes a hydrogel support 70 and sequencing-ready nucleic acid fragments 44" contained within the hydrogel support 70.

To form this complex 40C, a fluid containing hydrogel monomer(s) and/or polymer(s), radical source(s), and crosslinker(s) are mixed in the presence of the sample (e.g., genetic material). This fluid may be loaded into mineral oil or another suitable hydrophobic fluid, and emulsified to generate droplets. A radical initiator may be added to polymerize and/or crosslink the hydrogel monomer(s) and/or polymer(s) and form the hydrogel support 70.

Examples of suitable monomer(s) include acrylamide, N,N'-bis(acryloyl)cystamine, bisacrylamide, diacrylate, diallylamine, triallylamine, divinyl sulfone, ethyleneglycol diallyl ether, ethyleneglycol diacryate, trimethylolpropane trimethacrylate, ethoxylated trimethylol diacrylate, ethoxylated pentaerythritol tetracrylate, a collagen monomer, or combinations thereof.

Examples of suitable polymer(s) include polyethylene glycol-thiol, polyethylene glycol-acrylate, polyethylene glycol diacrylate, polyethylene glycol (e.g., having a weight average molecular weight ranging from about 100 to about 200,000), polypropylene oxide, polyacrylic acid, poly(hydroxyethyl methacrylate), poly(methyl methacrylate), poly(N-isopropylacrylamide), poly(lactic acid), poly(lactic-co-glycolic acid), polycaprolactone, poly(vinylsulfonic acid), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, a collagen polymer, or combinations thereof.

The radical source is a molecule that generates radicals when broken down. In an example, the radical source is selected from the group consisting of potassium persulfate, ammonium persulfate, 4,4'-azobis(4-cyanovaleric acid), 1,1'-azobis(cyclohexanecarbonitrile), azobisisobutyronitrile, 2,2'-azobis(2-methylpropionitrile), 2,2'-azobis(2-methylpropionitrile), peroxide, riboflavin, 3-(dimethylamino) propionitrile, and combinations thereof.

Examples of suitable crosslinkers may be reversible, in that they can be crosslinked and uncrosslinked depending on the chemical to which it is exposed. In example, the reversible crosslinker is a bisacrylamide crosslinker containing disulfide bonds, which can be broken down with reducing agents, such as DTT, TCEP, or THP (phosphine). In an example, the crosslinker is selected from the group consisting of acrylamide, N,N'-bis(acryloyl)cystamine, bisacrylamide, 1,4-diacroylpiperazine, N—N'-diallyl L-tartardiamide, and N—N'-(1,2-dihydroxyethylene)-bis-acrylamide. The initiator may be a photoinitiator (which initiates crosslinking upon exposure to light of an appropriate wavelength), or a radical initiator that initiates crosslinking when combined with the radical source. An example of this type of radical initiator is tetramethylethylenediamine (TEMED).

The sample becomes encapsulated within the hydrogel support because its size is sufficient that it cannot pass through the pores of the hydrogel bead. In some examples, the sample is DNA or RNA and is at least about 100 nucleotides in length (e.g., 1,000 nucleotides or more, 10,000 nucleotides or more, 500,000 nucleotides or more, etc.). In some examples, the pore size of the hydrogel support 70 refers to an average diameter or an average effective diameter of a cross-section of the pores, based on a measurement of a plurality of pores. The effective diameter of a cross-section that is not circular equals the diameter of a circular cross-section that has the same cross-sectional area as that of the non-circular cross-section. In an example, the pore size ranges from about 10 nm to about 100 nm.

Library preparation can then take place within the hydrogel support 70. Multiple reagent exchange may take place through the pores of the hydrogel support 70. The sample and any library fragments generated therefrom are maintained within the hydrogel matrix. Library preparation may involve fragmenting the sample and adding adapters that will result in sequence-ready fragments 44".

In an example, library preparation may be performed via tagmentation that takes place within the hydrogel support 70. The resulting complex 40C is shown in FIG. 12C. The adapter sequences include suitable adapters for bridge amplification and sequencing and thus the resulting fragments 44" are sequencing-ready. In another example, library preparation may be performed using polymerase extension, which results in a double stranded library. This example library needs to be denatured prior to release form the hydrogel support 70 and seeding.

Method Involving the Complexes

An example of the method disclosed herein utilizes an example of the flow cell 10A-10J disclosed herein and any one of the complexes 40A, 40B, or 40C. As described above, each of the complexes 40A, 40B, or 40C may include sequence-ready fragments obtained from the same sample of genetic material. When one or a few of the complexes 40A, 40B, or 40C are isolated within the respective chambers, spatial co-localization of the libraries from the same sample is achieved.

In this example method, the complexes 40A, 40B, or 40C are introduced into the flow cell 10A-10J, for example through one or more input ports. The complexes 40A, 40B, or 40C may be introduced with a fluid, such as Tris-HCl buffer or 0.5× saline sodium citrate (SSC) buffer.

Because the complexes 40A, 40B, or 40C are introduced in a fluid (e.g., an aqueous fluid), the hydrophobic barrier 20A-20J can help to improve the isolation of the complexes 40A, 40B, or 40C to the chambers 24 (which may be more hydrophilic than the hydrophobic barrier 20A-20J).

In each example flow cell 10A-10J, the thickness of the hydrophobic barrier 20A-20J above the interstitial regions 16 or the surfaces of the nano-pads 33 (and thus the depth of each chamber 24) is less than about 2 μm. With this shallow or non-existent depth, the capture site may be included to further aid in the immobilization of a single complex 40A, 40B, or 40C in a single chamber 24. While each chamber 24 may have one capture site, it is to be understood that some of the chambers 24 may not receive a complex 40A, 40B, or 40C during any given run of the method. Moreover, a single chamber 24 may include multiple capture sites. In this example, respective capture sites and complexes 40A, 40B, or 40C are members of a binding pair, so that one complex 40A, 40B, or 40C binds to one capture site within each of the chambers 24. More specifically, the capture sites may include the first member of the binding pair and each of the complexes 40A, 40B, or 40C may include the second member of the binding pair. As one specific example, the capture site is a capture site primer (e.g., a capture oligonucleotide), and each of the complexes 40A, 40B, or 40C includes a complementary primer that can hybridize to the capture site primer. As another specific example, the capture site may include avidin and biotin may be attached to the surface of the complex 40A, 40B, or 40C.

This example method then includes washing away non-immobilized complexes 40A, 40B, or 40C from the flow cell 10A-10J. Washing may involve introducing any suitable buffer into the flow cell 10A-10J. The flow may push any complexes 40A, 40B, or 40C that have not attached to the capture sites or are otherwise confined within a chamber 24 out through an exit port of the flow cell 10A-10J.

Some examples of the method then include introducing an external immobilization agent to the flow cell 10A-10J, and specifically, to the plurality of chambers 24. The external immobilization agent is air, or a liquid medium or a viscous medium that is not miscible with the complexes 40A, 40B, 40C, or 40D of the fluid that have been introduced to the flow cell chambers 24. Using air to aspirate the washing fluid out of the flow cell 10A-10J can create a liquid droplet that surrounds the complexes 40A, 40B, or 40C and forms a diffusion barrier. The liquid or viscous medium external immobilization agent at least partially surrounds the complexes 40A, 40B, or 40C that are attached within the chambers 24. In an example, the external immobilization agent sits on the fluid in the chambers 24. By at least partially surrounding the complexes 40A, 40B, or 40C, the external immobilization agent helps inhibit diffusion of the sequencing-ready nucleic acid fragments 44, 44', or 44" outside of the chambers 24 when the fragments 44, 44', or 44" are released.

It is to be understood that any of the external immobilization agents disclosed herein may be used, but in one example, the external immobilization agent is a liquid diffusion barrier selected from the group consisting of mineral oil and silicone oil, a viscous medium diffusion barrier selected from the group consisting of glycerol and sucrose, and combinations thereof. When the external immobilization agent is a temperature responsive material, raising the temperature to the seeding temperature may render the agent more viscous and in a form that can prevent library diffusion.

This example of the method then includes causing the carrier (e.g., the solid support 42 or the hydrogel support 70) of the trapped complexes 40A, 40B, or 40C to release the sequencing-ready nucleic acid fragments 44, 44', or 44" into the respective chamber 24 in which each immobilized complex 40A, 40B, or 40C is trapped. In this example, transport and seeding of the sequencing-ready nucleic acid fragments 44, 44', or 44" are restricted by the hydrophobic barrier 20A-20J and the external immobilization agent (if used).

Causing the carrier (i.e., support 42 or 70) to release the sequencing-ready nucleic acid fragments 44, 44', or 44" may vary, depending upon the complex 40A, 40B, or 40C that is used.

In some examples, the carrier is the solid support 42, and the causing involves introducing a cleaving agent to the flow cell 10A-10I. The cleaving agent may initiate chemical, enzymatic, or photo-chemical release of the sequencing-ready nucleic acid fragments 44 or 44' from the solid support 42. In these examples, another stimulus, such as heat or light, may trigger the cleaving agent to release the library fragments 44 or 44' from the solid support 42. As one example, free biotin may be introduced as the cleaving agent, and heating to about 92° C. may be used to induce biotin-oligo release from the solid support 42.

In other examples, the complex 40C is used and thus the carrier is the hydrogel support 70. In these other examples, causing library release may involve heating the flow cell 10A-10J, introducing a cleaving agent to the flow cell 10A-10J, or combinations thereof. Heating to release the library fragments 44" from the hydrogel support 70 may involve heating to a temperature of about 90° C. The entire flow cell 10A-10J may be heated, and when the complexes 40C heat up, the hydrogel support 70 may degrade to release the fragments 44". In some examples, the cleaving agent may include one or more components that can depolymerize the hydrogel support 70 and release the sequencing-ready fragments 44" therefrom. As examples, the cleaving agent includes dithiothreitol (DTT), tris-(2-carboxyethyl)phosphine (TCEP), or tris-(3-hydroxypropyl)phosphine (THP). In other examples, the cleaving agent is light. In these examples, the crosslinker used to form the hydrogel support 70 may include a photo-cleavable moiety, and exposure of the complexes 40C in the chambers 14 to light of an appropriate wavelength can cleave this moiety and degrade the hydrogel support 70.

As mentioned, transport and seeding of the sequencing-ready nucleic acid fragments 44, 44', or 44" in the example method are restricted by the hydrophobic barrier 20A-20J alone or in combination with the external immobilization agent. As such, the fragments 44, 44', or 44" of any particular complex 40A, 40B, or 40C will be confined to the chamber 24 to which the particular complex 40A, 40B, or 40C is confined because hydrophobic barrier 20A-20J, and in some instances, the external immobilization agent, at least partially surround the complex 40A, 40B, or 40C.

With the flow cells 10A-10J disclosed herein, the primers 36 in the nano-depressions 14 or on the nano-pads 33 can seed the released sequencing-ready nucleic acid fragments 44, 44', or 44". Seeding is accomplished through hybridization between the first or second sequence of the fragment 44, 44', or 44" and a complementary one of the primers 36 with the chamber 24. Seeding may be performed at a suitable hybridization temperature for the fragment 44, 44', or 44" and the primer(s) 36.

The location at which the sequencing-ready nucleic acid fragments 44, 44', or 44" seed within the respective chambers 24 depends, in part, upon the configuration of the nano-depressions 14 or the nano-pads 33. In these examples, the sequencing-ready nucleic acid fragments 44, 44', 44", or 44'" seed across the gel material 34 within each of the nano-depressions 14 of each of the nano-pads 33.

The seeded sequencing libraries can then be amplified using cluster generation.

In one example of cluster generation, the sequencing-ready nucleic acid fragments 44, 44', or 44" are copied from the hybridized primers 36 by 3' extension using a high-fidelity DNA polymerase. The original sequencing-ready nucleic acid fragments 44, 44', or 44" are denatured, leaving the copies immobilized within the chambers 24. Isothermal bridge amplification or some other form of amplification may be used to amplify the immobilized copies. For example, the copied templates loop over to hybridize to an adjacent, complementary primer 36, and a polymerase copies the copied templates to form double stranded bridges, which are denatured to form two single stranded strands. These two strands loop over and hybridize to adjacent, complementary primers 36 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template sequencing-ready nucleic acid fragments within each nano-depression 14 or on each nano-pad 33 within each chamber 24. This example of clustering is bridge amplification, and is one example of the amplification that may be performed. It is to be understood that other amplification techniques may be used, such as the exclusion amplification (ExAmp) workflow (Illumina Inc.).

After cluster generation, sequencing may be performed. Any example of the flow cell 10A-10J disclosed herein may be used in a variety of sequencing approaches or technologies, including techniques often referred to as sequencing-by-synthesis (SBS), cyclic-array sequencing, sequencing-by-ligation, pyrosequencing, and so forth.

As one example, a sequencing by synthesis (SBS) reaction may be run on a system such as the HISEQ™, HISEQX™, MISEQ™, MISEQDX™, MINISEQ™, NOVASEQ™, NEXTSEQDX™, NEXTSEQ™, or other sequencer systems from Illumina (San Diego, CA).

A sequencing primer may be introduced that hybridizes to a complementary sequence on the template polynucleotide strand. This sequencing primer renders the template polynucleotide strand ready for sequencing. In SBS, extension of sequencing primers along the template sequencing-ready nucleic acid fragment (the template polynucleotide strand) is monitored to determine the sequence of nucleotides in the templates. The 3'-ends of the templates and any flow cell-bound primers 36 (not attached to the copies) may be blocked to prevent interference with the sequencing reaction, and in particular, to prevent undesirable priming. The underlying chemical process can be polymerization (e.g., catalyzed by a polymerase enzyme) or ligation (e.g., catalyzed by a ligase enzyme).

In a particular polymerase-based SBS process, fluorescently labeled nucleotides are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide strand. For example, to initiate a first SBS cycle, one or more labeled nucleotides, DNA polymerase, etc., may be delivered into/through the flow cell 10A-10J, where sequencing primer extension causes a labeled nucleotide to be incorporated into a nascent strand that is complementary to the template. This incorporation can be detected through an imaging event. During an imaging event, an illumination system (not shown) may provide an excitation light to the flow cell 10A-10J.

In some examples, the fluorescently labeled nucleotides can further include a reversible termination property that terminates further primer extension once a nucleotide has been added to the template. For example, a nucleotide analog having a reversible terminator moiety can be added to the template such that subsequent extension cannot occur until a deblocking agent is delivered to remove the moiety. Thus, for examples that use reversible termination, a deblocking reagent can be delivered to the flow cell, etc. (after detection occurs).

Wash(es) may take place between the various fluid delivery steps. The SBS cycle can then be repeated n times to extend the template by n nucleotides, thereby detecting a sequence of length n.

While SBS has been described in detail, it is to be understood that the flow cells 10A-10J described herein may be utilized with other sequencing protocol, for genotyping, or in other chemical and/or biological applications.

To further illustrate the present disclosure, examples are given herein. It is to be understood that these examples are provided for illustrative purposes and are not to be construed as limiting the scope of the present disclosure.

EXAMPLES

Example 1

Examples of the flow cells disclosed herein were prepared in accordance with one of the methods described herein.

A glass substrate was utilized and had circular nano-depressions etched therein.

CYTOP® S was used as the hydrophobic polymer. The hydrophobic barrier extended from about 1 µm to about 2 µm in the Z-direction above the interstitial regions. The hydrophobic barrier also defined differently shaped chambers, such as circles with a diameter of 50 µm, squares with a width of 50 µm, crosses with a length and width of 50 µm each, and hexagons with a diagonal of 50 µm.

The gel material was PAZAM, and P5 and P7 primers were attached to the PAZAM.

A standard denatured PhiX control library (6 pM loading concentration) was added to each flow cell for seeding and cluster generation by bridge amplification. FIG. 13A through FIG. 13F illustrate the libraries in the nano-depressions in some of the chambers that were defined by the hydrophobic barriers. These images were taken after the DNA clusters inside the chamber geometries were stained with DNA intercalator dye (e.g., SYTOX). As observed in these figures, the chambers defined by the shallow hydrophobic barrier did not lead to any autofocus issues and no loss of library to the shallow sidewalls was observed.

Example 2

Glass substrates were coated with CYTOP® S to form a hydrophobic barrier as described in Example 1. The hydrophobic barrier had a thickness of about 2 pm, and the micro-chambers defined by the hydrophobic barrier had a diameter of about 40 µm. Three different hydrophobic barriers were formed, varying the pitch between the micro-chambers. The pitch varied from 1.15 to 1.5 times the diameter of the micro-chambers. The glass substrates were coated with PAZAM and polished to remove the gel material from the hydrophobic barriers. Primer grafting was performed to attach P5 and P7 primers to the PAZAM in the micro-chambers. A lid was bonded using a UV curable adhesive to form a flow cell.

A fluorescent dye containing liquid was introduced to the flow cells. Blue excitation wavelengths were emitted on the flow cells, and fluorescence images of the top of the flow cells were taken after the liquid was introduced. These images are shown as the top images at FIG. 14A(i), FIG. 14B(i), and FIG. 14C(i). As depicted, the liquid covered the surfaces, including the micro-chambers and the hydrophobic barriers.

The liquid was displaced with air at a flow rate of from about 200 µL/min (linear velocity of about 16 cm/s) to about 2 mL/min (linear velocity of about 80 cm/s). Blue excitation wavelengths were emitted on the flow cells, and fluorescence images of the top of the flow cells were taken after the air was introduced. These images are shown as the bottom images at FIG. 14A(ii), FIG. 14B(ii), and FIG. 14C(ii). As depicted, the introduction of air caused the liquid to become confined within the micro-chambers. The images in FIG. 14A(i) and (ii), FIG. 14B(i) and (ii) and FIG. 14C(i) and (ii) are at 20 times magnification.

Example 3

A flow cell was prepared as described in Example 1 with the hydrophobic barrier defining several circular micro-chambers around sub-sets of nano-depressions.

Complexes similar to those shown in FIG. 12A were prepared. The fragments on a particular bead were from the same long DNA molecule. The library fragments were attached to the solid support via a desthiobiotin oligo, which has weaker affinity than biotin. The complexes were loaded into the micro-chambers. Attachment of the complexes to the micro-chamber surface was accomplished with an anchor (e.g., complementary primers with biotin hybridized to the P5 primers attached to the gel material or alkyne-PEG-biotin linkers were covalently attached to free azides on the gel material using click chemistry). Free biotin in a saline sodium citrate buffer with sodium dodecyl sulfate was introduced and the flow cell was heated to about 80° C. to release the libraries from the respective complexes. Air was aspirated through the flow cell to push free biotin solution out. Due to the hydrophobic/hydrophilic surface structures, droplets were formed inside the micro-chambers when the liquid was pushed out by air. The droplets prevented the library fragments from diffusing to a neighboring micro-chamber.

The released library fragments were then hybridized to the surface primers in the micro-chambers, and an extension step was performed to create a complementary copy. Cluster generation was performed by bridge amplification. Sequencing was then performed on the flow cell.

Figure 15:
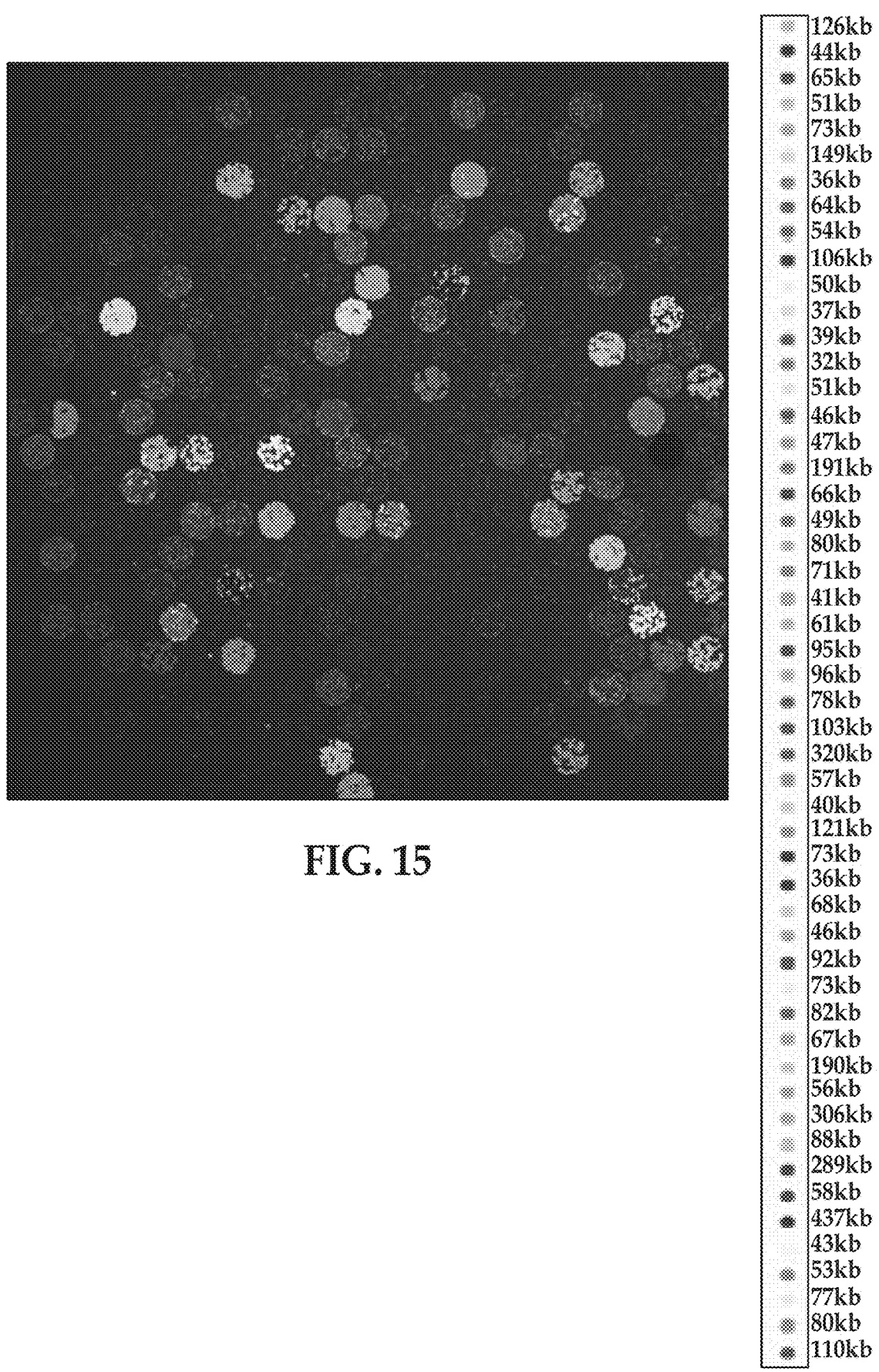
FIG. 15 is a black and white representation of an originally colored fluorescence microscopy image of different micro-chambers on an example flow cell after a sequencing run was performed.
Figure 17A:
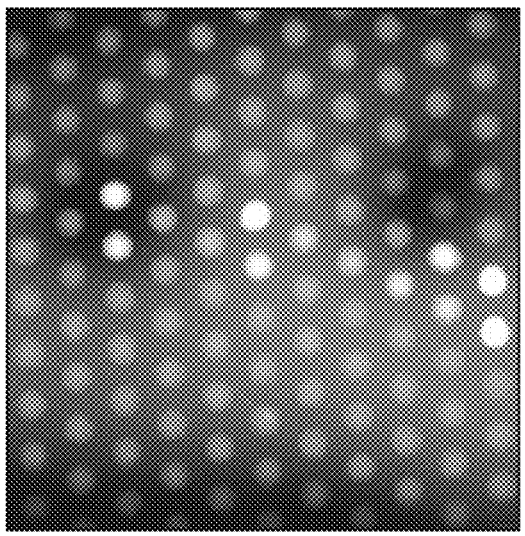
FIGS. 17A through 17D are black and white fluorescence microscopy images of different examples of the micro-chamber geometries defined by respective hydrophobic material layers having a thickness of about 200 nm, after aspiration was performed.
Figure 17B:
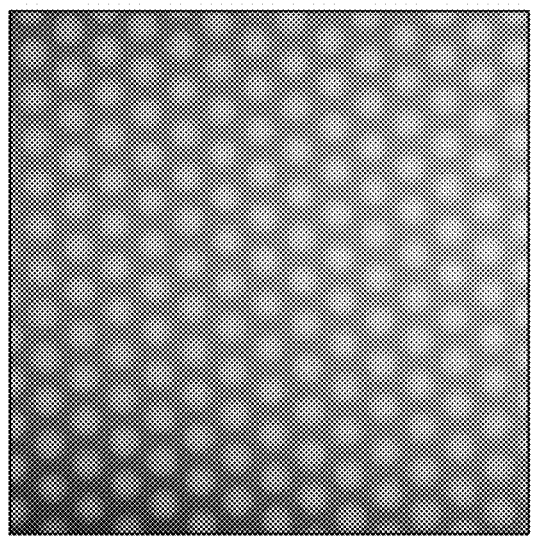
Figure 17C:
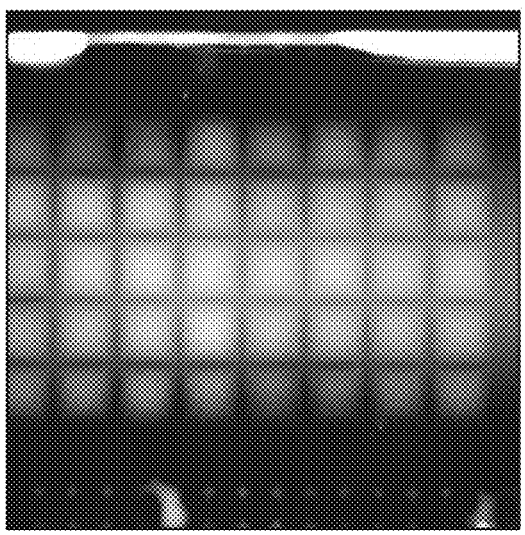
Figure 17D:
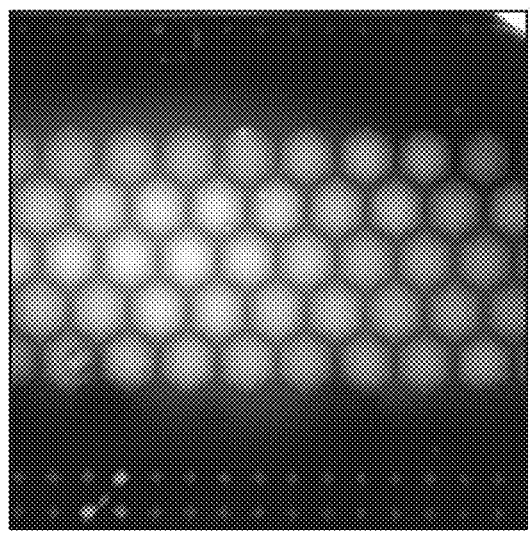

FIG. 15 illustrates a portion of the flow cell after data analysis of the sequencing run. The original colors represented an island, or short reads that were grouped together based on their proximity on the reference genome. Because the respective colors were isolated to a particular micro-chamber, it was concluded that the short reads in a given micro-chamber were from the same piece of genome DNA and thus from the same complex. These results indicate that the micro-chambers were able to confine the complexes and the released library fragments within the respective chambers.

Example 4

Glass substrates were coated with CYTOP® S to form a hydrophobic barrier as described in Example 1. The hydrophobic barriers had a thickness of about 1 µm, and the micro-chambers defined by the hydrophobic barrier had different shapes. The circular micro-chambers had a diameter of about 40 µm, and the square or hexagonal micro-chambers had a length and width or diagonal, respectively, ranging from about 180 µm to about 200 µm. The glass substrates were coated with PAZAM and polished to remove the gel material from the hydrophobic barriers. Primer grafting was performed to attach P5 and P7 primers to the PAZAM in the micro-chambers. A lid was bonded using a UV curable adhesive to form a flow cell.

A fluorescent dye containing liquid was introduced to the flow cells. The liquid was displaced with air at a flow rate of from about 200 µL/min (linear velocity of about 16 cm/s) to about 2 mL/min (linear velocity of about 80 cm/s). Blue excitation wavelengths were emitted on the flow cells, and fluorescence images of the top of the flow cells were taken after the air was introduced. These images are shown in FIG. 16A through FIG. 16E. As depicted, the introduction of air caused the liquid to become confined within the micro-chambers. The images in FIG. 16A through FIG. 16E are at 10 times magnification.

Example 5

Glass substrates were coated with CYTOP® S to form a hydrophobic barrier as described in Example 1. The hydrophobic barriers had a thickness of about 200 nm, and the micro-chambers defined by the hydrophobic barrier had different shapes. The circular micro-chambers had a diameter of about 40 µm, and the square or hexagonal micro-chambers had a length and width or diagonal, respectively, ranging from about 180 µm to about 200 µm. The glass substrates were coated with PAZAM and polished to remove the gel material from the hydrophobic barriers. Primer grafting was performed to attach P5 and P7 primers to the PAZAM in the micro-chambers. A lid was bonded using a UV curable adhesive to form a flow cell.

A fluorescent dye containing liquid was introduced to the flow cells. The liquid was displaced with air at a flow rate of from about 200 µL/min (linear velocity of about 16 cm/s) to about 2 mL/min (linear velocity of about 80 cm/s). Blue excitation wavelengths were emitted on the flow cells, and fluorescence images of the top of the flow cells were taken after the air was introduced. These images are shown in FIG. 17A through FIG. 17D. As depicted, the introduction of air caused the liquid to become confined within the micro-chambers. The images in FIG. 17A through FIG. 17D are at 10 times magnification.

Example 6

Examples of the flow cells disclosed herein were prepared in accordance with one of the methods described herein.

A glass substrate was utilized and had circular nano-depressions etched therein. The exposed nano-depressions were then silanized with norbornene and coated with the gel material, PAZAM. Polishing was performed to remove the PAZAM from the interstitial regions.

A positive photoresist was applied to the patterned substrate. The positive photoresist was exposed and developed to define a hexagonal pattern for the hydrophobic barrier. Oxygen plasma ashing was then performed to remove the norbornene and PAZAM from the patterned portion and to expose the patterned substrate in accordance with the hexagonal pattern.

Trichloro(1H,1H,2H,2H-perfluorooctyl)silane (PFOTS) was the hydrophobic material. The hydrophobic material was deposited across the positive photoresist and on the exposed portions of patterned substrate in accordance with the hexagonal pattern. A lift-off process was then used to remove the remaining photoresist and any hydrophobic material on the photoresist. This revealed the micro-chambers defined by the hydrophobic barrier and the sub-sets of nano-depressions within each micro-chamber. The hydrophobic barrier was a molecular monolayer coating the surface of the nanowells and the interstitial regions in the areas of the hexagonal pattern.

Primer grafting was performed to attach P5 and P7 primers to the PAZAM in the nano-depressions.

A CFR image of the flow cell surface was taken and is shown in FIG. 18A. This image shows that the PAZAM was effectively removed from the exposed portions of patterned substrate in accordance with the hexagonal pattern.

A fluorescein containing liquid was introduced to the flow cell. Air was then introduced into the flow cell at a flow rate of 100 µL/min to aspirate the liquid. FLUORINERT™ FC-40 (from 3M) was also introduced. Fluorescence images of the flow cell surface were taken after the FC40 oil was introduced. This image is shown in FIG. 18B. As depicted, the introduction of oil caused the fluorescein containing liquid to become confined within most of the micro-chambers. The results in FIG. 18A support that the hydrophobic material was successfully deposited.

Example 7

A dispersion of (tridecafluoro-1,1,2,2-tetrahydrooctyl) trichlorosilane in toluene was prepared. The concentration of the dispersion was 10%. The dispersion was printed on a glass substrate with an OPTOMEC AJ printer with 150 µm nozzles to form a hydrophobic barrier. The line width was about 20 µm. FIG. 19 depicts the printed hydrophobic barrier.

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A method, comprising:
   applying a hydrophobic material on a patterned substrate, the patterned substrate including:
      a plurality of sub-sets, each sub-set including:
         a plurality of nano-depressions defined in a surface of the patterned substrate; and
         interstitial regions separating the plurality of nano-depressions; thereby forming a hydrophobic material layer i) in the plurality of nano-depressions and ii) on the interstitial regions, wherein the hydrophobic material layer on the interstitial regions has a thickness less than about 2 µm;
   applying a mask material on a first portion of the hydrophobic material layer to define a pattern of a hydrophobic barrier around at least some of the plurality of sub-sets, whereby a second portion of the hydrophobic material layer is exposed at the at least some of the plurality of sub-sets;
   removing the second portion of the hydrophobic material layer, thereby exposing the at least some of the sub-sets;
   attaching a gel material to the nano-depressions of the at least some of the plurality of sub-sets; and
   removing the mask material from the first portion of the hydrophobic material layer to reveal the hydrophobic barrier.

2. The method as defined in claim 1, wherein:
   the patterned substrate further includes a barrier interstitial around each of the plurality of sub-sets;
   the pattern of the hydrophobic barrier is defined on the barrier interstitial and around each of the plurality of sub-sets; and
   the hydrophobic barrier is formed on the barrier interstitial.

3. The method as defined in claim 2, wherein:
   removing the second portion of the hydrophobic material layer involves etching the second portion of the hydrophobic material layer from each of the plurality of sub-sets; and
   removing the mask material involves exposing the mask material to a reagent.

4. The method as defined in claim 1, wherein the hydrophobic barrier fills the nano-depressions and extends on the interstitial regions of some other of the plurality of sub-sets that are positioned between the at least some of the sub-sets.

5. The method as defined in claim 4, wherein:
   removing the second portion of the hydrophobic material layer involves etching the second portion of the hydrophobic material layer from the at least some of the plurality of sub-sets, whereby the hydrophobic material layer remains over the other of the plurality of sub-sets; and
   removing the mask material involves exposing the mask material to a reagent.

6. The method as defined in claim 1, wherein:
   the attaching of the gel material involves:
      silanizing the nano-depressions and interstitial regions of the at least some of the sub-sets; and
      depositing the gel material on the nano-depressions and interstitial regions of the at least some of the sub-sets and on the mask material; and
   the method further comprises removing the gel material from the mask material and from the interstitial regions of the at least some of the sub-sets.

7. The method as defined in claim 1, wherein prior to applying the hydrophobic material, the method further comprises forming the patterned substrate by patterning a non-patterned support to form the plurality of nano-depressions of each of the plurality of sub-sets, and wherein the patterning involves etching, nano-imprint lithography, or combinations thereof.

8. The method as defined in claim 1, wherein:
   the removing of the mask material from the first portion of the hydrophobic material layer to reveal the hydrophobic barrier occurs prior to attaching the gel material; and
   attaching the gel material involves:
      silanizing the plurality of nano-depressions and interstitial regions of the at least some of the sub-sets; and
      depositing the gel material on the plurality of nano-depressions and interstitial regions of the at least some of the sub-sets and on the hydrophobic barrier; and
   the method further comprises removing the gel material from the hydrophobic barrier and from the interstitial regions of the at least some of the sub-sets.

9. The method as defined in claim 1, wherein the hydrophobic material layer has a thickness ranging from about 10 nm to about 1 µm.

10. The method as defined in claim 1, wherein the hydrophobic material is selected from the group consisting of a fluorinated polymer, a perfluorinated polymer, a silicon polymer, a silane, and a mixture thereof.

* * * * *